US006461616B1

(12) United States Patent
Montelaro et al.

(10) Patent No.: US 6,461,616 B1
(45) Date of Patent: Oct. 8, 2002

(54) EIAV P26 DELETION VACCINE AND DIAGNOSTIC

(75) Inventors: Ronald Montelaro, Wexford; Jodi Craigo, Pittsburgh, both of PA (US); Charles Issel, Lexington, KY (US); Bridget Puffer, Corning, NY (US); Kristina J. Hennessy; Karen K Brown, both of Parkville, MO (US)

(73) Assignee: Akzo Nobel NV, Arnhem (NL)

( * ) Notice: Subject to any disclaimer, the term of this patent is extended or adjusted under 35 U.S.C. 154(b) by 0 days.

(21) Appl. No.: 09/659,026

(22) Filed: Sep. 9, 2000

(51) Int. Cl.[7] ...................... A61K 39/193; A61K 39/12; A61K 39/00; C12Q 1/70

(52) U.S. Cl. ................................ 424/205.1; 424/204.1; 424/207.1; 424/208.1; 424/184.1; 435/5

(58) Field of Search ........................... 424/207.1, 184.1, 424/208.1, 204.1, 205.1; 435/5

(56) References Cited

U.S. PATENT DOCUMENTS 5,571,712 A * 11/1996 Haynes et al. ........... 435/240.2
5,674,720 A * 10/1997 Gorelick et al. ......... 435/172.3

OTHER PUBLICATIONS

Issel et al., Efficacy of Inactivated Whole–Virus and Subunit Vaccines in Preventing Infection and Disease Caused by Equine Infectious Anemia Virus, J. Virology, Jun. 1992, pp. 3398–3408.*

Fox, J., No winners against AIDS, Bio/Technology, vol. 12, Feb. 1994, p. 128.*

Haynes et al., Update on the Issues of HIV Vaccine Development, Finnish Medical Society DUODECIM, Ann Med, vol. 28, pp. 39–41.*

Fahey, et al., Status of immune–based therapies in HIV infection and AIDS, Clin. exp. Immunol. 1992, vol. 88, pp. 1–5.*

Virology, 161, pp. 321–331, Payne et al, Antigenic Variation and Lentrivirus Persistence: Variations in Envelope Gene Sequences during EIAV Infection Resemble Changes Reported for Sequential Isolates of HIV (month unavailable) 1987.

Salinovich, Olivia et al.: "Rapid Emergence of Novel Antigenic and Genetic Cariants of Equine infectious Anemia Virus during Persistent Infection", Virology, Jan. 1986, pp. 71–80, vol. 57, No. 1.

Hussain, K. A., et al.: "Antigenic mapping of the envelope proteins of equine infectious anemia virus: identification of a neutralization domain and a conserved region on glycoprotein 90", Archives of Virology, 1998, pp. 213–234.

Issel, C.J., et al.: "Efficacy of Inactivated Whole–Virus and Subunit Vaccines in Preventing Infection and Disease Caused by Equine Infectious Anemia Virus", Virology, Jun. 1992, pp. 3398–3408, vol. 66, No. 6.

(List continued on next page.)

*Primary Examiner*—Hankyel T. Park
*Assistant Examiner*—Stacy S. Brown
(74) *Attorney, Agent, or Firm*—William P. Ramey III

(57) ABSTRACT

Disclosed herein is a vaccine which provides immunity to mammals from infection and/or disease caused by a lentivirus, such as equine infectious anemia virus, human immunodeficiency virus (HIV), feline immunodeficiency virus (FIV), bovine immunodeficiency virus (BIV) or simian immunodeficiency virus (SIV) said composition comprising a deletion in a gene that blocks replication of the virus in vivo. Preferably said composition encompasses at least one deletion in a lentivirus which provides protection from exposure to wild-type lentiviruses. It also encompasses a marker vaccine in which a foreign gene is inserted into the gene-deleted region, said inserted gene providing a diagnostic tool for use in vaccinated mammals. The scope of the invention encompasses an EIAV vaccine that allows equines to be safely vaccinated and protected from disease without converting to a seropositive status on the Coggin's Test or any other test which measures p26.

11 Claims, 14 Drawing Sheets

OTHER PUBLICATIONS

Orrego, Alberto et al.: "Virulence and in vitro growth of a cell–adapted strain of equine infectious anemia virus after serial passage in ponies", American Journal of Veterinary Research, 1982, pp. 1556–1560, vol. 43, No. 9.

Hammond, Scott A. et al.: "Maturation of the Cellular and Humoral Immune Responses to Persistent Infection in Horses by Equine Infectious Anemia Virus is a Complex and Lengthy Process", Virology, May 1997, pp. 3840–3852, vol. 71, No. 5.

Cook, R. Frank et al.: "Development and Characterization of an In Vivo Pathogenic Molecular Clone of Equine Infectious Anemia Virus", Virology, Feb. 1998, pp. 1383–1393, vol. 72, No. 2.

Leroux, Caroline et al.: "Novel and Dynamic Evolution of Equine Infectious Anemia Virus Genomic Quasispecies Associated with Sequential Disease Cycles in an Experimentally Infected Pony", Virology, Dec. 1997, pp. 9627–9639, vol. 71, No. 12.

Langemeier, John L., et al.: "Detection of Equine Infectious Anemia Viral RNA in Plasma Samples from Recently Infected and Long–Term Inapparent Carrier Animals by PCR", Journal of Clinical Microbiology, Jun. 1996, pp. 1481–1487, vol. 34, No. 6.

Lichtenstein, Drew L., et al.: "Genomic Quasispecies Associated with the Initiation of Infection and Disease in Ponies Experimentlly Infected with Equine Infectious Anemia Virus", Virology, Jun. 1996, p. 3346–3354, vol. 70, No. 6.

Lichtenstein, Drew L., et al.: "Replication In Vitro and In Vivo of and Equine Infectious Anemia Virus Mutant Deficient in dUTPase Activity", Virology, May 1995, pp. 2881–2888, vol. 69, No. 5.

Ball, Judith M., et al.: "Detailed Mapping of the Antigenicity of the Surface Unit Glycoprotein of Equine Infectious Anemia Virus by Using Synthetic Peptide Strategies", Virology, Feb. 1992, pp. 732–742, vol. 66, No. 2.

Montelaro, Ronald C., et al.: "Antigenic Variation during Persistent Infection by Equine Infectious Anemia Virus, a Retrovirus", Journal of Biological Chemistry, Aug. 1984, pp. 10539–10544, vol. 259, No. 16.

Issel, Charles J., et al.: "A Perspective on Equine Infectious Anemia with an Emphasis on Vector Transmission and Genetic Analysis", Veterinary Microbiology, 1998, pp. 251–286.

Ball, Judith M., et al.: "EIAV Genomic Organization: Further Characterization by Sequencing of Purified Glycoproteins and cDNA", Virology, 1988, pp. 601–605.

Issel, Charles J., et al.: "Evolution of Equine Infectious Anemia Diagnostic Tests: Recognition of a Need for Detection of Anti–EIAV Glyucoprotein Antibodies", pp. 196–200 (1988).

Rwambo, P.M., et al.: "In vitro isolation of a neutralization escape mutant of equine infectious anemia virus (EIVA)", Archives of Virology, 1990, pp. 275–280.

Rwambo, P.M., et al.: "Equine infectious anemia virus (EIAV) Humoral responses of recipient ponies and antigenic variation during persistent infection", Archives of Virology, 1990, pp. 199–212.

Newman, Mark J., et al.: "Transient Suppression of Equine Immune Responses by Equine Infectious Anemia Virus (EIAV)", Virology, May 1991, pp. 55–66.

Montelaro, Ronald C., et al.: "Immunologic management of equine infectious anemia virus: a model for AIDS vaccine development", Eds. H. Schellenkens and M.C. Horzinek Animal models in AIDS, 1990 Elsevier Science Publishers B.V. (Biomedical Division) pp. 221–232.

Hammond, Scott A., et al.: "Immune Responses and Viral Replication in Long–Term Inapparent Carrier Ponies Inoculated with Equine Infectious Anemia Virus", Virology, Jul. 2000, pp. 5968–5981, vol. 74, No. 13.

Tencza, Sarah B., et al.: "Development of a Fluorescence Polarization–Based Diagnostic Assay for Equine Infectious Anemia Virus", Journal of Clinical Microbiology, May 2000, pp. 1854–1859, vol. 38, No. 5.

Harrold, Sharon M., et al.: "Tissue Sites of Persistent Infection and Active Replication of Equine Infectious Anemia Virus during Acute Disease and Asymptomatic Infection in Experimentally Infected Equids", Virology, Apr. 2000, pp. 3112–2121, vol. 74, No. 7.

Li, Feng, et al.: "The S2 Gene of Equine Infectious Anemia Virus Is a Highly Conserved Determinant of Viral Replication and Virulence Properties in Experimentally Infected Ponies", Virology, Jan. 2000, pp. 573–579, vol. 74, No. 1.

Raabe, Michelle L., et al.: "In Vitro Antibody–Dependent Enhancement Assays Are Insensitive Indicators of in Vivo Vaccine Enhancement of Equine Infectious Anemia Virus", Virology, 199, pp. 416–427.

Hammond, Scoctt A., et al.: "A Particulate Viral Protein Vaccine Reduces Viral Load and Delays Progression to Disease in Immunized Ponies Challenged with Equine Infectious Anemia Virus", Virology, 1999, pp. 37–49.

Li, Feng, et al.: The S2 Gene of Equine Infectious Anemia Virus Is Dispensable for Viral Replication In Vitro, Virology, Oct. 1998, pp. 8344–8348, vol. 72, No. 10.

Raabe, Michelle, et al.: Immunization with a Recombinant Envelope Protein (rgp90) of EIAV Produces a Spectrum of Vaccine Efficacy Ranging from Lack of Clinical Disease to Severe Enhancement, Virology, 1998, pp. 151–162.

Payne, S.L., et al.: "Characterization of infectious molecular clones of equine infectious anaemia virus", Journal of General Virology, 1994, pp. 425–429.

Wang, S.Z.–S. et al.: "Enhancement of EIAV Replication and Disease by Immunization with a Baculovirus–Expressed Recombinant Envelope Surface Glycoprotein", Virology, 1994, pp. 247–251.

Costa, L.R., et al.: "Responses of Ponies to Challenge with Equine Infectious Anaemia Virus Following Exposure to Recombinant gp90 or Viral p26 Immunogens", Equine Infectious Diseases VII, pp. 85–94 (1994).

Grund, Christian H., et al.: "Fine specificity of equine infectious anaemia virus gp90–specific antibodies associated with protective and enhancing immune responses in experimentally infected and immunized ponies", Journal of General Virology, 1996, pp. 435–442.

Montelaro, Ronald C., et al.: "Vaccines against Retroviruses", The Retroviridae, vol. 4, 1995, Chapter 8, pp. 605–656.

* cited by examiner

Schematic representation of EIA virus $EIAV_{UK}$

Circular Map of Infectious Clone EIAV$_{UK}$

EcoRI 0
MluI 166
BstXI 831
SspI 13310
PstI 12751
AmpR
NruI 11536
AvaI 11081
EIAV$_{UK}$
13498 bp
S2
Bpu1102I 2735
NcoI 3409
ori
DU
PvuII 8484
MluI 8143
SstI 5257

Linear Schematic of the Molecular Clone $EIAV_{UK}$

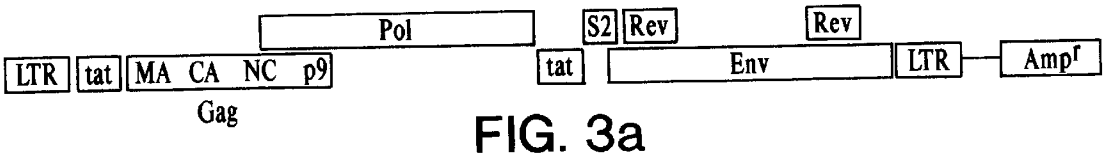

FIG. 3a

Linear Schematic of Molecular Clone $EIAV_{UK}$ with the CMV Promoter

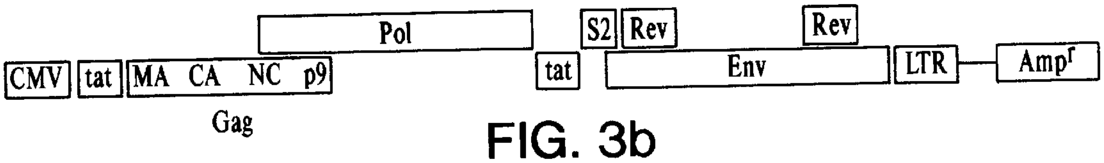

FIG. 3b

Linear Schematic of Molecular Clone $EIAV_{UK}$ with the CA gene deleted

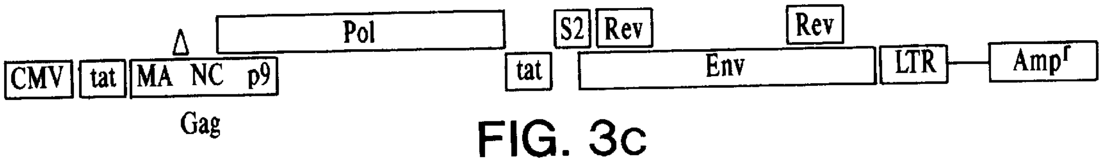

FIG. 3c

Linear Schematic of Molecular Clone $EIAV_{UK}$ with the Amp Resistance Gene Replaced by the Kanamycin Resistance Gene

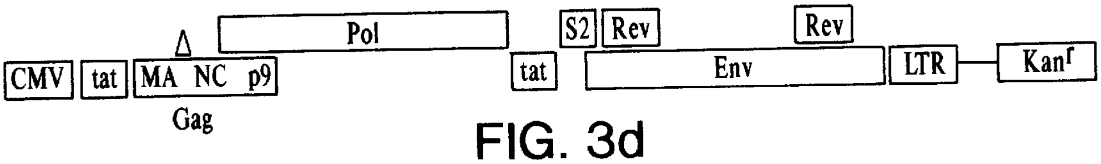

FIG. 3d

Linear Schematic of the p26 Deleted Proviral Clone pCMV.ΔCA.neo

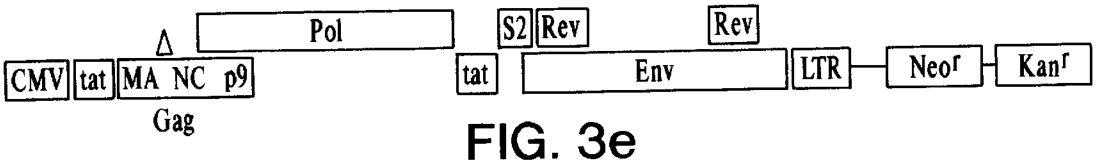

FIG. 3e pCMV.ΔCA.neo --15494 bp

Linear Schematic Representation of $EIAV_{UK}$

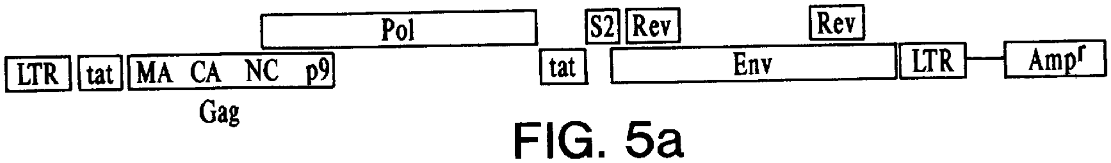

FIG. 5a

Linear Schematic Representation of the $EIAV_{UK}$ clone with the CMV promoter insert ($CMVEIAV_{UK}$)

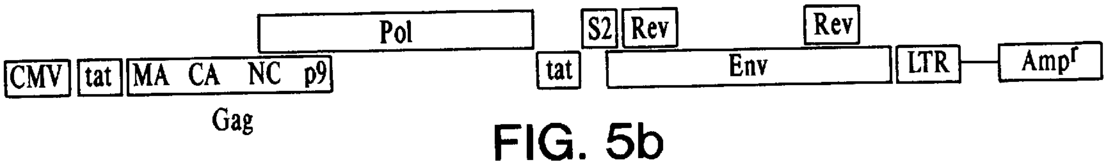

FIG. 5b

Linear Schematic Representation of the $CMVEIAV_{UK}$.vis2.

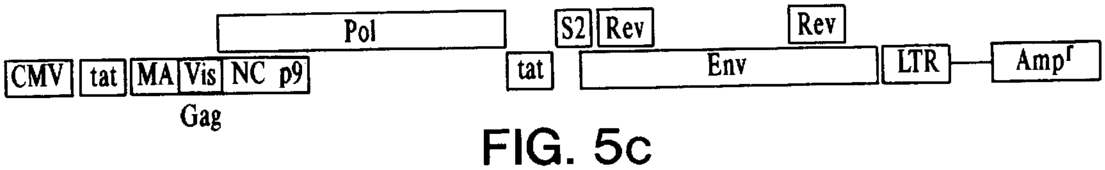

FIG. 5c

Linear Schematic Representation of the Proviral Clone containing the Kanamycin Resistance Marker.

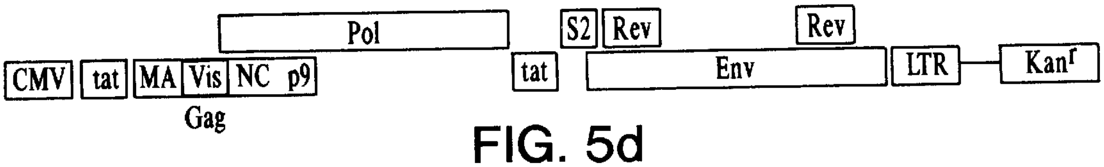

FIG. 5d

Linear Schematic Representation of the final pCMV.Vis2.neo Proviral Construct

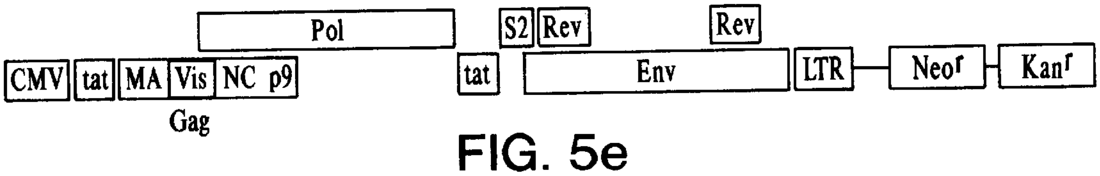

FIG. 5e

Circular map of the final pCMV.Vis2.neo Proviral Construct.

Nucleotide and Amino Acid Map of the Capsid Antigen Gene/EIA Virus p26 Protein

```
10 20 30 40 50 60 70
CCAATCATGATAGATGGGGCTGGAAACAGAAATTTTAGACCTCTAACACCTAGAGGATATACTACTTGGGTGAATACC
P I M I D G A G N R N F R P L T P R G Y T T W V N T

80 90 100 110 120 130 140 150
ATACAGACAAATGGTCTATTAAATGAAGCTAGTCAAAACTTATTTGGGATATTATCAGTAGACTGTACTTCTGAAGAA
I Q T N G L L N E A S Q N L F G I L S V D C T S E E

160 170 180 190 200 210 220 230
ATGAATGCATTTTTGGATGTGGTACCTGGCCAGGCAGGACAAAAGCAGATATTACTTGATGCAATTGATAAGATAGCA
M N A F L D V V P G Q A G Q K Q I L L D A I D K I A

240 250 260 270 280 290 300 310
GATGATTGGGATAATAGACATCCATTACCGAATGCTCCACTGGTGGCACCACCACAAGGGCCTATTCCCATGACAGCA
D D W D N R H P L P N A P L V A P P Q G P I P M T A

320 330 340 350 360 370 380 390
AGGTTTATTAGAGGTTTAGGAGTACCTAGAGAAAGACAGATGGAGCCTGCTTTTGATCAGTTTAGGCAGACATATAGA
R F I R G L G V P R E R Q M E P A F D Q F R Q T Y R

400 410 420 430 440 450 460
CAATGGATAATAGAAGCCATGTCAGAAGGCATCAAAGTGATGATTGGAAAACCTAAAGCTCAAAATATTAGGCAAGGA
Q W I I E A M S E G I K V M I G K P K A Q N I R Q G

470 480 490 500 510 520 530 540
GCTAAGGAACCTTACCCAGAATTTGTAGACAGACTATTATCCCAAATAAAAAGTGAGGGACATCCACAAGAGATTTCA
A K E P Y P E F V D R L L S Q I K S E G H P Q E I S

550 560 570 580 590 600 610 620
AAATTCTTGACTGATACACTGACTATTCAGAACGCAAATGAGGAATGTAGAAATGCTATGAGACATTTAAGACCAGAG
K F L T D T L T I Q N A N E E C R N A M R H L R P E

630 640 650 660 670 680
GATACATTAGAAGAGAAAATGTATGCTTGCAGAGACATTGGAACTACAAAACAAAAGATGATGTT
D T L E E K M Y A C R D I G T T K Q K M M L
```

FIG. 7

Nucleotide and Amino Aacid Map of the CA gene/Visna Virus p30

```
         10        20        30        40        50        60        70
CCTATTGTGAATTTGCAAGCAGGAGGGAGAAGTTGGAAGGCGGTAGAGTCAGTAGTCTTCCAGCAACTGCAAACAGTG
P  I  V  N  L  Q  A  G  G  R  S  W  K  A  V  E  S  V  V  F  Q  Q  L  Q  T  V

 80        90        100       110       120       130       140       150
GCAATGCAGCATGGACTTGTGTCCGAGGATTTTGAGAGGCAATTGGCATATTATGCTACTACCTGGACTAGTAAAGAT
A  M  Q  H  G  L  V  S  E  D  F  E  R  Q  L  A  Y  Y  A  T  T  W  T  S  K  D

   160       170       180       190       200       210       220       230
ATATTAGAAGTATTGGCTATGATGCCTGGGAATAGAGCACAGAAGGAATTAATACAAGGAAAATTAAATGAAGAAGCA
I  L  E  V  L  A  M  M  P  G  N  R  A  Q  K  E  L  I  Q  G  K  L  N  E  E  A

     240       250       260       270       280       290       300       310
GAAAGGTGGGTAAGACAAAATCCACCCGGGCCGAATGTCCTCACGGTGGATCAAATAATGGGAGTGGGACAAACCAAT
E  R  W  V  R  Q  N  P  P  G  P  N  V  L  T  V  D  Q  I  M  G  V  G  Q  T  N

     320       330       340       350       360       370       380       390
CAGCAGGCATCTCAAGCCAATATGGATCAGGCAAGACAGATATGCCTGCAGTGGGTAATAACAGCGTTAAGATCAGTG
Q  Q  A  S  Q  A  N  M  D  Q  A  R  Q  I  C  L  Q  W  V  I  T  A  L  R  S  V

         400       410       420       430       440       450       460
AGGCATATGTCACATAGACCAGGAAACCCTATGTTAGTGAAGCAGAAGAATACTGAGAGTTATGAAGACTTCATAGCT
R  H  M  S  H  R  P  G  N  P  M  L  V  K  Q  K  N  T  E  S  Y  E  D  F  I  A

 470       480       490       500       510       520       530       540
CGCCTACTAGAGGCTATTGATGCGGAACCAGTGACGGACCCTATAAAAACATATTTAAAAGTAACATTGTCATATACA
R  L  L  E  A  I  D  A  E  P  V  T  D  P  I  K  T  Y  L  K  V  T  L  S  Y  T

   550       560       570       580       590       600       610       620
AATGCTAGCACAGACTGTCAAAAGCAGATGGATAGGACATTGGGGACGAGGGTTCAACAAGCAACGGTAGAAGAAAAG
N  A  S  T  D  C  Q  K  Q  M  D  R  T  L  G  T  R  V  Q  Q  A  T  V  E  E  K

    630       640       650       660       670
ATGCAAGCATGTCGAGATGTGGGATCCGAAGGATTTAAGATGCAATTA
M  Q  A  C  R  D  V  G  S  E  G  F  K  M  Q  L
```

FIG. 8

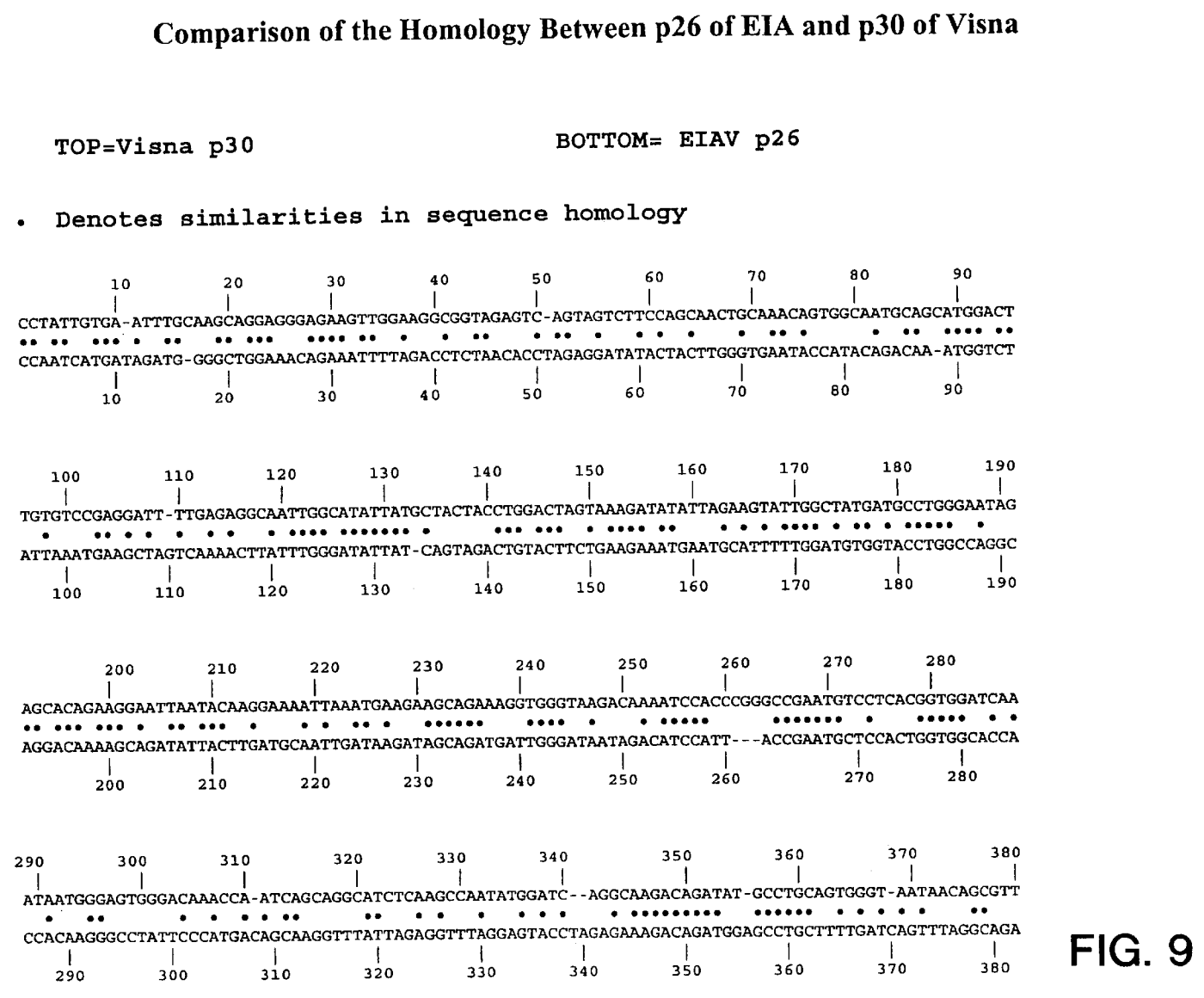

Comparison of the Homology Between p26 of EIA and p30 of Visna

TOP=Visna p30          BOTTOM= EIAV p26

• Denotes similarities in sequence homology

```
            10         20         30         40         50         60         70         80         90
            |          |          |          |          |          |          |          |          |
CCTATTGTGA-ATTTGCAAGCAGGAGGAAGTTGGAAGGCCGTAGTC-AGTAGTCTTCCAGCAACTGCAAACAGTGGCAATGCAGCATGGACT
•••·••••·  ····  •• ·  ····  ····••  ·•• ··         · ·• ··•  · ··  · ··••·  •   ·••••
CCAATCATGATAGATG-GGGCTGGAAACAGAAATTTTAGACCTCTAACACCTAGAGGATATACTTGGGTGAATACCATACAGACAA-ATGGTCT
            |          |          |          |          |          |          |          |
            10         20         30         40         50         60         70         80         90

           100        110        120        130        140        150        160        170        180        190
            |          |          |          |          |          |          |          |          |          |
TGTGTCCGAGGATT-TTGAGAGGCAATTGGCATATTATGCTACTACCTGACTAGTAAAGATATTAGAAGTATTGGCTATGATGCCTGGGAATAG
··•····  ··••    ·•••  ······   ·      ···  ···  ·····   ·····   ···•     · ·••••    ······
ATTAAATGAAGCTAGTCAAAACTTATTTGGGATATTAT-CAGTAGACTGTACTTCTGAAGAAATGAATGCATTTTTGATGTGTACCTGCCAGGC
            |          |          |          |          |          |          |          |          |
           100        110        120        130        140        150        160        170        180        190

           200        210        220        230        240        250        260        270        280
            |          |          |          |          |          |          |          |          |
AGCACAGAAGGAATTAATACAAGGAAAATTAAATGAAGCAGATATTGGGTAAGACAAAATCACCCGGGCCGAATGTCCTCACGGTGATCAA
•••·••·    ·····   ·· •• · ···    ·•••     ·····     ····                 ······  ·····
AGGACAAAAGCAGATATTACTTGCAATTGATAGTAAGATAGCAGATGATTGGGATAATAGACATCCATT---ACCGAATGCTCCACTGGTGCACCA
            |          |          |          |          |          |          |          |          |
           200        210        220        230        240        250        260        270        280

           290        300        310        320        330        340        350        360        370        380
            |          |          |          |          |          |          |          |          |          |
ATAATGGGAGTGGGACAAACCA-ATCAGCAGGCATCTTCAAGCCAATATGGATC--AGGCAAGACAGATAT-GCCTGCAGTGGGT-AATAACAGCGTT
·•··            ·••    ·•·            ·•·••••••        ·•·••••••        ·•·••••         ··
CCACAAGGGCCTATTCCCATGACAGCAAGGTTTATTAGAGTTTAGGAGTACCTAGAAAAGACAGATGAGCCTGCTTTTGATCAGTTAGCAGA
            |          |          |          |          |          |          |          |          |
           290        300        310        320        330        340        350        360        370        380
```

FIG. 9

```
390 400 410 420 430 440 450 460 470
AAGATCAGTGAGGCATA-TGTCACATAGACCAGGAAACCCTATGTTAGTGA--AGCAGA---AGAATACTGAGAGTTATG-AAGACTTCATAGCTCG
• •• • • ••• • • • ••• • • • • ••• • • • • • • • ••• • ••• • • •
CATATAGACAATGGATAATAGAAGCCATGTCAGAAGGCATCAAAGTGATGATTGGAAAACCTAAAGCTCAAAATATTAGGCAAGGAGCTAAGGAACC
390 400 410 420 430 440 450 460 470

480 490 500 510 520 530 540 550 560
CCTACTAGAGGCTATTGATGCGGAACCAGTGACGGACCCTATA-AAAACATATTTAAAAGTAACATTGTCATATACAAATGCTAGCACAGACTGT-C
• ••• • • •• • • • • • • • • •• • ••• • • •• • •• •• ••• •••• • •
TTACCCAGAATTTGTAGACAGACTATTA-TCCCAAATAAAAAGTGAGGGACATCCACAAGAGATTTCAAAATTCTTGACTGATA-CACTGACTATTC
480 490 500 510 520 530 540 550 560 570

570 580 590 600 610 620 630 640 650
AAAA-GCAGATGGATAGGACATTGGGG--ACGAGG-GTTCAACA----AGCA-ACGGTAGAAGAAAAGATGCAAGCATGTCGAGATGTGGGATCCGA
• •• ••• ••• • • • • ••• •• •• • •• • •• ••••••• •• ••• • •• •• •••• • ••• •
AGAACGCAAATGAGGAATGTAGAAATGCTATGAGACATTTAAGACCAGAGGATACATTAGAAGAGAAAATGTATGCTTGCAGAGACATTGGAACTAC
580 590 600 610 620 630 640 650 660 670

660 670
AGGATTTAAGATGCAATTA
• • •••••• ••
AAAACAAAAGATGATGTT-
680
```

FIG. 9 Cont'd

Western Blot of EIA Virus Constructs

Anti-EIA α-gp90 & α-p26 Monoclonal Antibody

Western Blot of EIA Virus Constructs

Anti-Goat α-Visna p30 Monoclonal Antibody

| | Falcon | | | | Non-Falcon | | | | Subclones | | | |
|---|---|---|---|---|---|---|---|---|---|---|---|---|
| | Vis 1 | Vis 2 | ΔCA 1 | ΔCA 2 | Vis 1 | Vis 2 | ΔCA 1 | ΔCA 2 | V2.14 V2.23 | V2.12 | V2.2 | PV–1μg |

213 —
135 —
85 —

44 —

18.5 —

Reverse Transcriptase Activity of Subclones of Tissue Culture Cells Transfected with pCMV.Vis2.neo Proviral Construct RT-Activity of Subclones

| RT-ACTIVITY: CPMs/10ul SUPERNATANT | | | | | | | |
|---|---|---|---|---|---|---|---|
| | | 24-WELL → | 6-WELL → | T75 Flask → | T75 Flask → | T75 Flask → | T75 Flask |
| | | Day 0 | Day 5 | Day 15 | Day 19 | Day 27 | Day 34 |
| F-1 | **V2.14** | 1455 | 6369.15 | 14189.3 | 22973.75 | 16707.65 | 19385.3 |
| F-1 | **V2.23** | 3935 | 10546.3 | 39419.8 | 42406.3 | 51359.65 | 40679.9 |
| NF-1 | **V2.12** | 3949 | 2356.6 | 12893.6 | 22674.1 | 9718.25 | 13917.1 |
| NF-1 | **V2.22** | 2126 | 5038.4 | 13082.5 | 7555.15 | 11742.75 | |
| NF-2 | **V2.2** | 1488 | 5603.65 | 35601.4 | 23058.55 | 21449.45 | 10287.75 |
| NF-2 | **V2.7** | 2184 | 4505.4 | 19891.8 | 11956.25 | 14822.05 | |
| NF-2 | **V2.13** | 1965 | 3647.45 | 12355.2 | 13411.7 | 12935.65 | |
| NF-2 | **V2.20** | 2602 | 5951 | 22832.1 | 16424.1 | 19846.15 | |

Chimeric Virus-Like Particles from V2.23 Cell Line
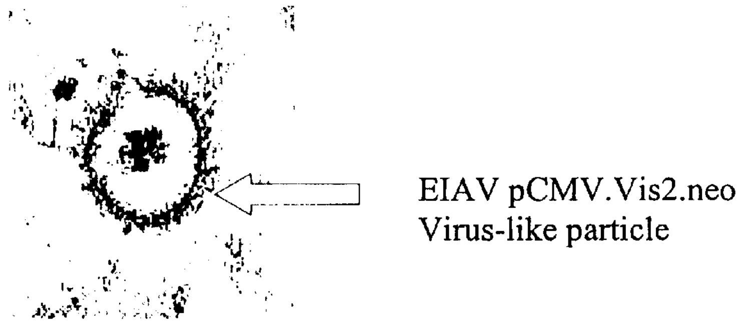
Budding from the ED MCS cells:
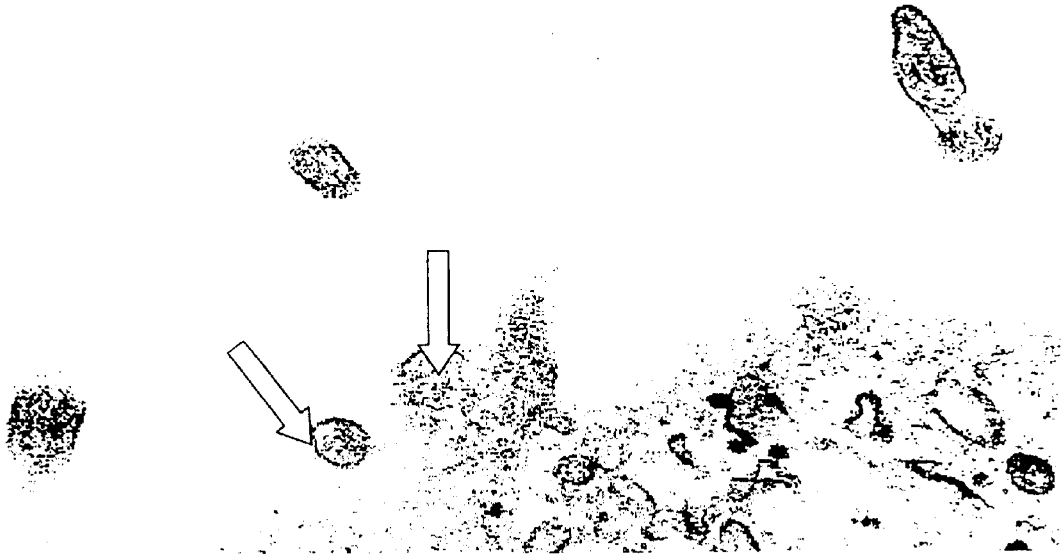
FIG. 12

EIAV P26 DELETION VACCINE AND DIAGNOSTIC

BACKGROUND OF THE INVENTION

1. Field of the Invention

This invention pertains to a vaccine composition which provides immunity from clinical disease signs and/or infections caused by lentiviruses including but not limited to Equine Infectious Anemia Virus (EIAV), Human Immunodeficiency Virus (HIV), Feline Immunodeficiency Virus (FIV), Bovine Immunodeficiency (BIV) and Simian Immunodeficiency Virus (SIV) or any other similar lentivirus. More specifically, but without limitation hereto, the invention relates to an Equine Infectious Anemia Virus (EIAV) composition which provides immunity from clinical disease signs and/or infection with EIAV, and which composition allows diagnostic differentiation between vaccinated and non-vaccinated but exposed or diseased mammals, and which allows the vaccinated animal to test negative using a Coggins test or other similar test that detects p26-specific antibodies 2. Brief Description of the Prior Art Lentiviruses are a subfamily of retroviruses that cause persistent infection and chronic disease in numerous types of mammals including humans (HIV), equines (EIA), felines (FIV), bovines (BIV) and monkeys (SIV). All of the diseases are spread by blood transmission. EIAV causes persistent infection and chronic disease in horses world wide. With EIAV, the blood transmission occurs by biting flies and other insects carrying virus particles from one horse to another. The first cycle of disease (clinical episode) in an infected horse usually occurs within 42 days after exposure to the virus. This first cycle is usually referred to as the acute stage of EIA and is characterized by pyrexia, thrombocytopenia, anorexia, depression and high plasma viremia levels. Anemia is not usually detected at this stage. Resolution of this first febrile episode is normally observed after 1 to 5 days and occurs concomitantly with a dramatic drop in the amount of plasma-associated virus. Following the acute stage, some animals may remain clinically normal while others go on to experience multiple bouts of illness in which severe anemia may accompany pyrexia, thrombocytopenia, edema, and dramatic weight loss, and death. In instances of persistent infection by a lentivirus, as illustrated by EIAV, nucleotide sequence data has revealed a high mutation rate of the lentivirus genome as reported by Payne et al, Virology, 1987: 161, p. 321–331 which is incorporated herein by reference. With EIAV infections, it is generally thought that neutralizing antibodies aid in the selection of new antigenic virus variants during persistent infections. Also, with EIAV infections, serologically distinct variants of EIAV emerge possibly through immune selection pressure operating on random viral genome mutations. Without being bound to any particular theory, it is believed that horses that show no further clinical signs of disease have developed a mature immune response that can protect against the virus and its known mutations.

As a member of the lentivirus subfamily of retroviruses, EIAV is useful as a model for the pathogenicity, immunology, vaccinology, treatment and prevention of HIV. The disease is significant in its own right because horses that demonstrate exposure to EIAV as measured by testing for anitbodies in the blood (Coggins Test or similar p26 detecting test) are either required to be destroyed or strictly quarantined. As a result of the Coggins Test requirement and its broad use throughout the world, especially in testing performance horses that are transferred into and out of the United States, it is critical that any effective EIA vaccine not be able to seroconvert horses to a positive Coggins Test or to any other test that detects p26. Therefore, for vaccines useful in protecting against EIA, it is important to either delete all or part of the gene expressing p26 or block its expression by deleting regulator genes or inserting stop codons or foreign genes. It is expected that use of the methods described herein can provide vaccines for the other lentiviruses (HIV, FIV, BIV and SIV) that can elicit immune responses that are effective and that can be distinguished from viral infections.

As with other lentiviruses such as HIV, BIV, FIV and SIV, the genetic organization of EIAV classifies it as a complex retrovirus. The EIAV genome contains the canonical gag, pol, and env genes common to all retroviruses, and three accessory genes (S1, S2 and S3). The gag gene encodes the core proteins of the virus designated as Matrix Antigen (MA), Capsid Antigen (CA), Nucleocapsid (NC) and a protein designated p9. The env gene encodes the viral envelope proteins (gp90 and gp45). The pol gene encodes the enzymes that replicate the viral genome, designated as Deoxy UTPase (DU), Reverse Transcriptase (RT) and Integrase (IN). The S1 open reading frame (ORF) encodes the viral Tat protein, a transcription trans activator that acts on the viral long-terminal-repeat (LTR) promoter element to stimulate expression of all viral genes. The S3 ORF encodes the Rev protein, a post-transcriptional activator that acts by interacting with its target RNA sequence, named the Rev-responsive element (RRE), to regulate viral structural gene expression. The S2 gene is located in the pol-env intergenic region immediately following the second exon of Tat and overlapping the amino terminus of the Env protein (see FIG. 1). It encodes a 65 amino acid protein with a calculated molecular mass of 7.2 kDa. S2 appears to be synthesized in the late phase of the viral replication cycle by ribosomal leaky scanning of a tricistronic mRNA encoding Tat, S2 protein, and Env protein, respectively.

The gag-encoded Capsid Antigen (CA) or p26 protein comprises the capsid shell of the virion that is enclosed in the viral envelope and that contains the viral RNA genome. Homologous CA proteins are present in HIV, FIV, BIV and SIV and are also encoded by the respective gag genes. As noted above, detection of antibodies to the p26 antigen is the basis for the Coggins Test and certain other commercial tests used to diagnose EIA in horses. To be compatible with current regulatory guidelines, it is critical that any EIAV vaccine not stimulate seroconversion in these diagnostic assays based on detection of serum antibodies to EIAV p26. The p26 antigen is highly antigenic in that extremely small amounts of its presence in a vaccine can stimulate antibody responses and seroconversion in diagnostic assays. Attempts to extract or delete p26 antigen from a pool of EIAV have not been practical for vaccine production. Therefore, it would seem that one could eliminate it by deletion of the gag gene, a segment of the gag gene that interferes with the expression of p26 or deletion or inactivation of a control gene that regulates the expression of p26. However, it has been determined by the inventors that deletion of the gag gene or segments thereof produces an EIAV particle that is unable to replicate in vitro (tissue culture) or in vivo. Therefore, simply deleting or blocking expression of p26 makes growth of EIAV for vaccine production impractical if not impossible.

To provide protection from disease and protection from infection, envelope proteins (Env) are considered the proteins of choice, as these proteins are the predominant immune targets during infection. By protection from disease is meant that a mammal exposed to the virus does not demonstrate clinical signs (fever, lethargy, anemia, death, etc.), but does carry virus particles in its blood, which particles are detectable by a reverse transcriptase polymerase chain reaction test (RT-PCR). By protection from infection is meant that a mammal exposed to the virus does not demonstrate clinical signs of EIA and does not contain RT-PCR-detectable virus particles in blood. The major envelope proteins of EIAV are gp90 and gp45. These are proposed as the protective antigens or protective components of EIAV. By the term protective components is meant antigens from that produce either protection from disease or protection from infection as indicated above. It is therefore important that any effective lentivirus vaccine contain amounts of the lentiviral Env proteins (such as gp 120, gp90 or gp45) effective to protect mammals from disease caused by the lentivirus. The protective components from EIAV include but are not limited to gp90 and gp45. The Capsid Antigen (p26) is not a protective component of EIAV and, because of its ability to stimulate a significant antibody response, the vaccine of the present invention preferably lacks the ability to stimulate p26 antibodies in an equid.

It would seem obvious to prepare a vaccine by purifying out the Env proteins, especially gp90 and gp45 for EIAV. Indeed, vaccines comprising preparation from which gp90 and gp45 have been purified out of the EIAV have been attempted with extremely limited success. Issel et al (J. Virol. June 1992, p 3398–3408) reports that a gp90/gp45 vaccine protected ponies from infection caused by homologous EIAV (the subunits were derived from the same EIAV strain as was used for challenge). However, these subunit-containing vaccines did not protect horses from either disease or infection when challenged with a heterologous EIAV strain. In fact, the latter produced enhanced disease signs. The enhancement of disease by the subunit EIAV vaccine corroborates findings with SIV and FIV subunit vaccines that appear to enhance disease post challenge. Issel et al (ibid) concludes that perfecting a subunit vaccine for lentiviruses (e.g., HIV, FIV, EIA, BIV and SIV) poses a significant challenge because of the subunit enhancement effect.

Issel, et al (ibid) also reports the prevention of infection by a whole-virus EIAV vaccine. However, vaccination of horses with this vaccine produces horses that are Coggins Test positive (p26 positive). As mentioned previously, due to the eradication program in effect in the U.S., horses testing positive for p26 are either euthanized or strictly quarantined. Additionally, the amount of virus included in said vaccine was 1 milligram, an amount not commercially feasible. Therefore, this whole-virus vaccine is not compatible with regulatory requirements or commercialization.

A donkey virus vaccine has been in use by the Chinese for more than 20 years. This vaccine was developed by using total EIAV genetic material from donkey leukocyte attenuated EIAV infected cells and ribonucleic acid from virus in peripheral blood of donkey-adapted EIAV from infected donkeys (see Xinhua News Agency, May 6, 1999). As would be expected, this vaccine produces a p26 positive response (Coggin's Test positive) in vaccinated horses or other vaccinated equids. Such a vaccine is not acceptable in those countries where equids are tested by Coggins assays or other p26-specific antibody tests. In addition, numerous countries will not accept live vaccines for veterinary applications.

Since there has been no effective and safe method for immunizing mammals against disease or infection caused by lentiviruses, particularly equines against EIA, and since lentivirus diseases, especially HIV, FIV and EIA are such a wide-spread and significant diseases world-wide, there remains a long-felt need to prepare such a vaccine.

The vaccine of this invention provides a successful vaccine composition that effectively and safely immunizes mammals from diseases caused by lentiviruses. The vaccine of the present invention protects equines from EIA wherein vaccinated equines can be differentiated from wild-type infected equines, which does not convert said equines to Coggins Test positive and which does not replicate in vivo. It is fully envisioned that the vaccines taught by the present invention can be used for production of any lentivirus vaccines, including vaccines for HIV, FIV, BIV and SIV.

DESCRIPTION OF THE FIGURES

FIG. 3*a* is a linear schematic of the molecular clone $EIAV_{UK}$

FIG. 3*b* is a linear schematic of molecular clone $EIAV_{UK}$ with the CMV promoter.

FIG. 3*c* is a linear schematic of molecular clone $pCMVEIAV_{UK}$ with the CA gene deleted.

FIG. 3*d* is a linear schematic of molecular clone $pCMVEIAV_{UK}\Delta CA$ with the Amp Resistance gene replaced by the Kanamycin Resistance gene.

FIG. 3*e* is a linear schematic of the p26-deleted Proviral Clone pCMV.ΔCA.neo.

FIG. 5*a* is a linear schematic of the $EIAV_{UK}$ molecular clone.

FIG. 5*b* is a linear schematic representation of the $EIAV_{UK}$ clone with the CMV promoter insert ($CMVEIAV_{UK}$).

FIG. 5*c* is a linear schematic representation of the $PCMVEIAV_{UK}$.vis2.

FIG. 5*d* is a linear schematic representation of the Proviral Clone containing the Kanamycin Resistance Marker.

FIG. 5*e* is a linear schematic representation of the final $pCMVEIAV_{UK}$.Vis2.neo Proviral Construct.

FIG. 7 is the nucleotide and amino acid map of the CA gene/EIAV p26.

FIG. 8 is the nucleotide and amino acid map of the CA gene/Visna p30.

FIG. 9 is a comparison of the homology between p26 of EIAV and p30 of Visna virus.

SUMMARY OF THE INVENTION

Figure 1:
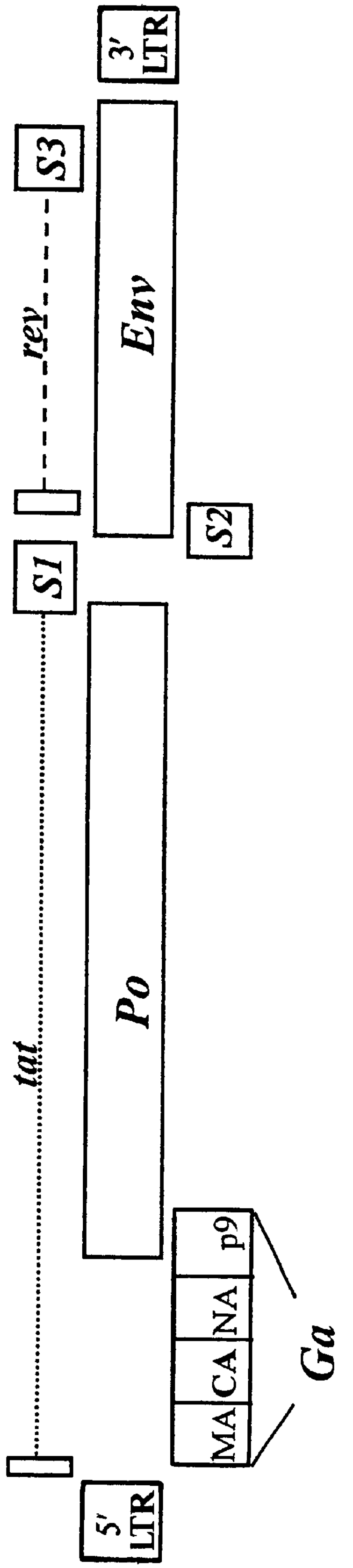
FIG. 1 is a schematic representation of EIAV designated $EIAV_{UK}$

This invention encompasses a safe and effective vaccine that produces immunity to mammals from infection and/or disease caused by a lentivirus. Examples of the lentivirus can be equine infectious anemia virus, human immunodeficiency virus (HIV), feline immunodeficiency virus (FIV), bovine immunodeficiency virus (BIV) or simian immunodeficiency virus (SIV) said vaccine comprising a deletion in the gene encoding the Capsid Antigen. More specifically, the invention encompasses a vaccine comprising a deletion that produces a lack of ability of the lentivirus to express the Capsid Antigen and to replicate in vivo while retaining the lentivirus protective components. Also, the vaccine allows differentiation between vaccinated and non-vaccinated, but exposed, mammals and provides safety and immunity when administered as a vaccine to mammals. By the term safe is meant that vaccination with of mammals with vaccines of the present invention does not produce infection, disease or any other adverse reaction in the vaccinated mammals. Said vaccine encompasses at least one deletion in a lentivirus, which allows mammals to be safely vaccinated and provides protection from exposure to wild-type lentiviruses. The invention further encompasses a lentivirus with a deletion in the gag gene, specifically a deletion that results in an inability of the lentivirus to express the Capsid Antigen (CA protein) in vivo or in vitro. Finally, the EIAV vaccine of the present invention lacks the ability to stimulate p26 antibodies in an equid.

In a preferred embodiment, the invention encompasses a vaccine for effectively and safely immunizing mammals from EIA, said composition comprising a gene-deleted EIAV construct wherein said gene-deleted construct interrupts virus replication in vivo and blocks the expression of p26 in vivo while retaining the EIAV protective components. As such, vaccinated equines would be protected from disease caused by EIAV and not convert to a seropositive status on the Coggins Test or any other test that measures p26 antibodies. As used herein, the term EIA refers to the disease Equine Infectious Anemia and the term EIAV refers to the Equine Infectious Anemia Virus that causes the disease. Additionally, said EIAV vaccine cannot cause clinical disease in mammals or spread or shed to other mammals including equines.

A more specific embodiment of the invention is a vaccine wherein the lack of ability to express p26 antigen results from one or more gene deletions within the gag gene, one or more deletions within a gene having a regulatory effect on gag CA production, an insertion of one or more stop codons into the gag CA gene or a gene regulating CA production, or insertion of a foreign gene into the gag CA gene or a gene regulating CA production. By insertion of a foreign gene is meant that the gene being inserted is not a gene associated with EIAV. Said foreign gene is obtained from a non-EIAV organism.

Additionally, it is expected that further deletions could be made such that the EIAV in the vaccine contained multiple deletions including but not limited to a deletion in the gag gene affecting the expression of p26.

Finally, it is expected that said gene deletions (deleted regions) could serve as potential points for insertion of foreign genes to produce a multiple-protective vaccine. This means that a single vaccination with the EIAV vaccine carrying a foreign gene (e.g., influenza hemagglutinin (HA) gene) could protect the mammal from both the lentivirus disease (e.g., HIV or EIA) and the disease associated with the foreign gene insert (e.g., human or equine influenza).

DETAILED DESCRIPTION OF THE INVENTION

This invention provides a vaccine for effectively and safely immunizing mammals against diseases caused by lentiviruses selected from the group consisting of EIAV, HIV, FIV, BIV and SIV, said vaccine comprising a gene-deleted lentivirus construct. The invention encompasses a vaccine comprising a deletion that produces a lack of ability of the lentivirus to replicate in vivo and retains the lentivirus protective components. By lentivirus protective components is meant the protective antigens associated with the envelope of the lentiviruses including but not limited to gp120, gp90 and gp45. The invention encompasses a lentivirus that is unable to express the Capsid Antigen (CA protein) in vivo.

A deletion can be produced in the lentivirus genome by using specific restriction endonucleases to remove all or part of one or more genes. A preferred gene for removal is the gene encoding the Capsid Antigen (CA). Such gene deletion can be accomplished by using PCR, ligation and PCR cloning; to delete the selected gene sequence. Restriction endonucleases can also be used to remove specific portions of genes once the gene sequence of the lentivirus and the gene sequence of the gene to be excised are known. Using specific restriction endonucleases, the gag gene can be removed in whole or part. Additionally, a stop codon can be inserted into the gene, preferably at the 5' end wherein the stop codon causes the gene not to express its CA protein. Additionally, a foreign gene from another lentivirus or an unrelated virus can be inserted into the gene-deleted region producing a multiply protective vaccine. In the latter case, the invention describes the deletion of a region of the EIAV genome large enough to insert a gene expressing a protective antigen from a non-EIAV organism, preferably a virus. Therefore, the HA gene from equine influenza A2 or A1 can be inserted into the gag CA region allowing expression of gp90 and gp45 of EIAV as well as HA of A1 and A2 equine influenza. This will provide a vaccine that can protect from disease in equines caused by EIAV and equine influenza viruses. Also, genes from equine herpes viruses types 1, 2, and 4 can be inserted into the EIAV construct to provide protection against disease of equines caused by EIAV and equine herpes viruses. Other equine viruses which could have genes encoding for protective antigens inserted in the EIAV include but are not limited to equine arteritis, encephalomyelitis viruses (Eastern, Western, Venezuelan and Rift Valley Fever virus). Genes encoding protective antigens from parasites (*Sarcocystis neurona* that causes Equine Protozoal Encephalitis or EPM, *Neospora heugesi* that is also possibly related to EPM, *Toxoplasma gondii,* etc.) can also be inserted into an EIAV construct to protect against these diseases. Finally, genes encoding for bacterial diseases of horses, including but not limited to *Streptococcus equi* and *Clostridium tetani,* can be inserted into an EIAV construct to provide multiple disease protection. It is expected that even a gene encoding for an immunostimulatory protein (immunomodulator gene) or glycoprotein can be inserted into the gene-deleted region in order to enhance the immunity provided by the virus construct.

Broadly described, a method for deleting a gene of a lentivirus (e.g. the CA gene) and insertion of a foreign gene utilizes the techniques of PCR, ligation, and a method of PCR cloning.

Primers are designed to amplify a region of a promoter-lentivirus genome upstream of the CA open reading frame (ORF). Additional primers are used to amplify the region of the promoter-lentivirus genome downstream of the CA. The amplified PCR products are purified using agarose gel electrophoresis and ligated together. A final round of PCR is performed using the 5' primer of the upstream fragment, and the 3' primer of the downstream fragment, followed by gel purification. The final product would comprise a representative size of the gag gene with a deletion of the CA open reading frame. The PCR product is gel purified and digested with specified restriction endonucleases such that it can be ligated with a plasmid that had been digested with the same restriction enzymes or enzymes producing the same blunt ends. The ligated insert is preferably added to a lentivirus clone comprising a promoter and genes allowing for selection of clones (e.g., antibiotic resistance genes) thus producing a promotor-lentivirus clone. Then the promoter-lentivirus clone is transformed into competent bacterial cells and colonies of the bacteria are screened for insertion of the genes. Clones may be genetically sequenced to verify that the CA region had been deleted and an insert had been made.

A gene-deleted construct could be commercially produced (produced in large scale) by transfecting susceptible tissue culture cells, harvesting the fluids and formulating the fluids with an adjuvant. Optionally, the harvest fluids may be inactivated with art-known inactivating agents such as formalin, binary ethyleneimine, beta-propiolactone, thimerasol and psoralen. By gene-deleted construct is meant a lentivirus in which a gene is non-functional due to a deletion, an insertion of a stop codon, or production of a gene insertion in which the deleted gene is replaced by a gene from another virus.

If said gene-deleted lentivirus cannot replicate in vitro, tissue culture cells may be transfected with the construct using transfecting agents such as DEAE dextran, GeneP-ORTER™ (Gene Therapy Systems), etc., to incorporate the necessary genomic material into the cell DNA such that the cells produce lentivirus antigens. For transfection, tissue culture cells are seeded into wells of tissue culture vessels (e.g. plates), exposed to the gene-deleted construct or the gene-deleted/gene-inserted construct in the presence of a transfecting agent, incubated to allow transfection and then overlayed with a selection medium. Selection media is defined as any nutrient medium that contains components to kill non-transfected cells but does not inhibit growth of transfected cells. To accomplish this, generally, gene-deleted constructs contain inserts of a resistance gene in order to allow the construct to grow in said selection media. Selection media can contain antibiotics, antimicrobials and selective antibiotics. Once transfected cells have been selected and are replicating they are tested for production of protective antigens as well as for the absence of expression of the deleted gene product. Those clones demonstrating these characteristics are then expanded in selection media by removing the cells from their initial container, diluting them and replanting them into larger containers. For instance, initial transfection may be carried out in 24 well tissue culture plates. After selection of clones, the surviving transfected cells are passaged to 6 well plates, 25 $cm^2$ flasks, 75 $cm^2$ flasks and then to roller bottles (1700 $cm^2$ or larger). Transfected cells should consistently produce the virus construct, indicating a stable transfected or producer cell. After the transfected cell clones have been demonstrated to be stable, stable-transfected Master Cells (also referred to as persistently infected cells by various regulatory agencies) can be prepared for expansion into Working Cells and Production Cells. Working Cells are defined as those cells that are used to prepare Production Cells. Production Cells are the cells used to manufacture vaccines. Master Cells, Working Cells and Production Cells are all generally stored in liquid nitrogen for retaining viability and stability of the transfecting clone.

In the practice of this invention, a vaccine comprising a gene-deleted construct lacks the ability to replicate in vivo and, possibly, in vitro. As should be realized by the foregoing, this type of deletion, if producing an inability to replicate or grow in vitro, requires transfection and cloning as described above.

The following is an illustrative but non-limiting description of a lentivirus that is unable to express the Capsid Antigen protein (CA or p26) in vivo. It has been determined that with EIAV, a deletion in the CA such that the p26 is not expressed results in a gene-deleted construct that cannot replicate in vitro or in vivo. For this reason, it is expected that such a CA deleted lentivirus would have to be produced in a stable transfected cell line. This means that it would have to be transfected as described above in order to produce the stable transfected cell line.

This invention more specifically encompasses a vaccine wherein the lack of ability to express p26 antigen is produced by one or more gene deletions within the gag gene or one or more deletions within a gene having a regulatory effect on gag CA production, or an insertion of one or more stop codons or insertion of a foreign gene.

It is expected that further deletions could be made such that the EIAV in the vaccine composition contained multiple deletions including but not limited to a deletion in the gag gene affecting the expression of p26. Finally, it is expected that said gene deletions (deleted regions) could served as potential points for insertion of foreign genes to produce a multiply-protective vaccine and a very important feature for EIAV, a marker vaccine. A marker vaccine is a vaccine that contains a foreign gene that produces antibody in the mammal receiving a vaccination, said antibody being detected by a diagnostic test and being used to distinguish a vaccinated equid from a non-vaccinated equid and a vaccinated equid from an infected equid. With EIAV, it is preferred to insert a CA gene from a different lentivirus that does not cross-react with p26 in the Coggins Test or equivalent tests. Therefore, insertion of the p30 gene from a different lentivirus such as a Visna virus would be expected to allow an EIAV vaccine to be used for vaccination of mammals, preferably equids. Said equids would demonstrate no p26 antibody in the Coggins Test or any other test measuring the presence of antibody to p26 antibodies, and would, additionally, demonstrate antibody to p30 which could be detected by an enzyme linked immunosorbant assay (ELISA), immunodiffusion test, fluorescent antibody test (FA), or any other test that can be used to detect antibodies in mammals.

It is expected that the gag gene-deleted constructs discussed above will not grow or replicate in vitro. Therefore, in order to produce large quantities for manufacturing purposes, the cloned constructs can either be expressed by bacterial cells or by mammalian cells (tissue culture). The process of transformation has been described briefly above and is described in detail in the EXAMPLES. Production of a stable transfected tissue culture cell line (persistently infected Master Cell) is preferable and is accomplished by transfecting mammalian cells in tissue culture. A preferred technique for EIAV constructs is described in the examples to follow.

The resulting p26 deleted construct can be employed in a vaccine for effectively and safely immunizing equines from EIAV, said vaccine comprising a gene-deleted EIAV construct wherein said gene deletion blocks the expression of p26 in vivo.

Vaccine viruses or virus constructs of this invention can be further treated with inactivating agents such as formalin, beta propiolactone, binary ethyleneimine, thimerasol or any other that effectively inactivates viruses. Such agents can be used in amounts varying from 0.00001% to 0.5%, preferably from 0.00001% to 0.1% and more preferably from 0.00001% to 0.01%.

Additionally, adjuvants or immunomodulators/immunostimulators may be added to the vaccine to enhance the immune response produced by the vaccine. Adjuvants can be selected for the group consisting of polymers such as Carbopol®-based, HAVLOGEN® and POLYGEN®, block co-polymers, oil-in-water such as EMULSIGEN® or EMULSIGEN® PLUS, water-in-oil, aluminum salts, lipid-based, lipoprotein, endotoxin-based and combinations thereof. Immunomodulators and imuno-stimulators include but are not limited to *Corynebacteria pyogenes* and extracts or subunits thereof, parapox viruses and extracts or subunits thereof, modified live viruses that stimulate interferon production, as well as cytokines.

The vaccines of this invention can be administered by any route. For instance, they can be administered intramuscularly, subcutaneously, intradermally, intranasally, orally, intravenously or intraperitoneally. It is preferable to administer the vaccines either intramuscularly, subcutaneously, orally or intranasally.

Other antigens may be added to the vaccines such that a multi-component vaccine can be produced. In order to accomplish this, antigens from other viruses, bacteria or parasites are formulated with adjuvants or other excipients and then combined with the EIAV construct of this invention. Therefore, this invention encompasses an EIAV construct combined with antigens from the group selected from equine influenza (A1 and A2), equine herpes virus (subtypes 1, 2, 3 or 4), equine arteritis virus, eastern equine encephalomyelitis, western equine encephalomyelitis, Venezuelan equine encephalitis, Rift Valley Fever Virus, *Sarcocystis neurona, Neospora hugesi, Toxoplasma gondii, Giardia lamblia, Streptococcus equi, Streptococcus zooepidemicus, Rhodococcus equi, Clostridium botulinum, Clostridium tetani, Clostridium difficile* or any other equine disease-producing agent. The *Clostridium botulinum* can include types A, B, C, D, E, and/or F.

Finally, it is within the scope of this invention that a diagnostic test can be used to differentiate vaccinated equines from non-vaccinated and/or infected equines by measuring the presence or absence of antibodies to the deleted gene protein. Also, a PCR-based diagnostic test could be used to detect the presence or absence of the genes or gene sequences in body fluids or tissues from the equine and, thus, detect whether an equine had been infected with EIAV or vaccinated with the composition of this invention. The diagnostics of choice measure the presence or absence of p26 antibodies in an equine. Additionally, if an inserted gene is from a non-equine organism such as a Visna virus, a protein product of the non equine organism could be measured. An example described herein includes the insertion of the p30 gene from Visna virus wherein the p30 can be detected in vaccinated equines but is not present in non-vaccinated or EIAV infected equines.

Diagnostic differentiation can be measured by developing an immunoassay, an antibody-detecting assay (e.g., indirect fluorescent antibody, immunodiffusion, agar diffusion, electrophoresis) or a PCR-based assay known to the art. An example of an immunoassay is an enzyme linked immunosorbant assay (ELISA) that detects and/or quantitates antibodies to specific proteins in serum, blood or tissues. ELISA technology could also be used to detect the presence or absence of virus-associated antigens in the blood, serum or tissues. By virus-associated antigens is meant the presence or absence of a gene expression product such as the p26 protein of EIAV or p30 protein of Visna virus or in the case of the p26 or p30 genes, respectively. PCR-based assays have been used to measure the presence or absence of genes or gene sequences in the blood, serum or tissues of an equine, thus indicating that a horse had been infected or vaccinated, as the case may be. For this particular embodiment, an ELISA would detect the presence of antibodies to the p26 or p30 proteins. If p26 antibodies were present in horses that were tested it would indicate that the horse had been infected with EIAV. Horses that had been vaccinated with a gene-mutated EIAV construct containing a non-functional p26 gene would not contain p26 antibodies in their serum. Horses that had been vaccinated with a gene-mutated EIAV construct containing a p30 gene insertion would contain p30 antibodies in their serum. Thus, vaccinated horses could be differentiated from infected horses. The PCR-based assays would be used to detect the presence or absence of gene sequences within the horse. For instance, if a horse had been infected with a wild-type EIAV, it would contain the gene sequence for wild-type p26. However, equines immunized with vaccines comprising a gene-mutated EIAV, particularly one wherein the p26 gene comprised deletions or specific mutations would not contain the gene sequence for wild-type p26. Alternatively, horses that had been vaccinated with a gene deleted EIAV construct containing a p30 gene insertion would contain the p30 gene sequence in their serum.

These and other aspects of the invention are further illustrated by the following non-limiting examples. In the examples and throughout the specification, parts are by weight unless otherwise indicated.

EXAMPLE 1

Figure 2:
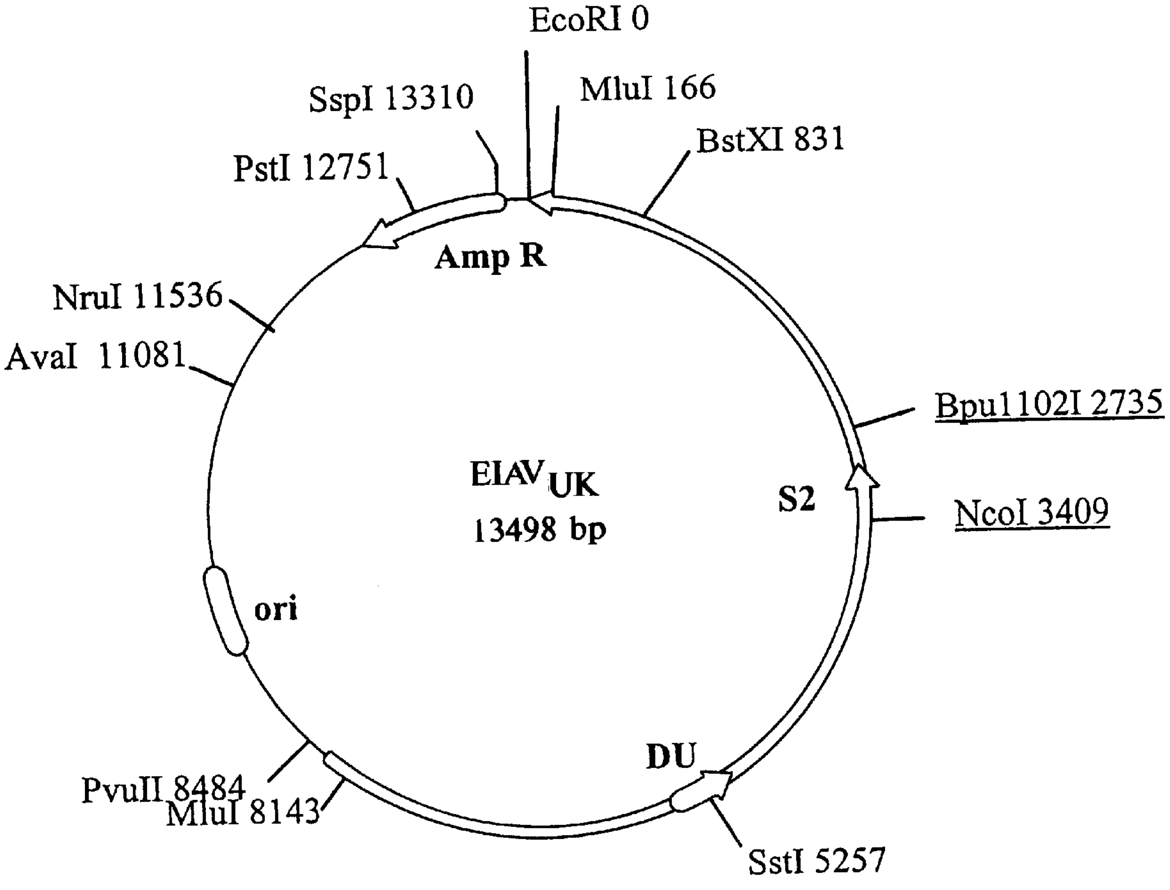
FIG. 2 is a circular map of infectious clone $EIAV_{UK}$
Figure 6:
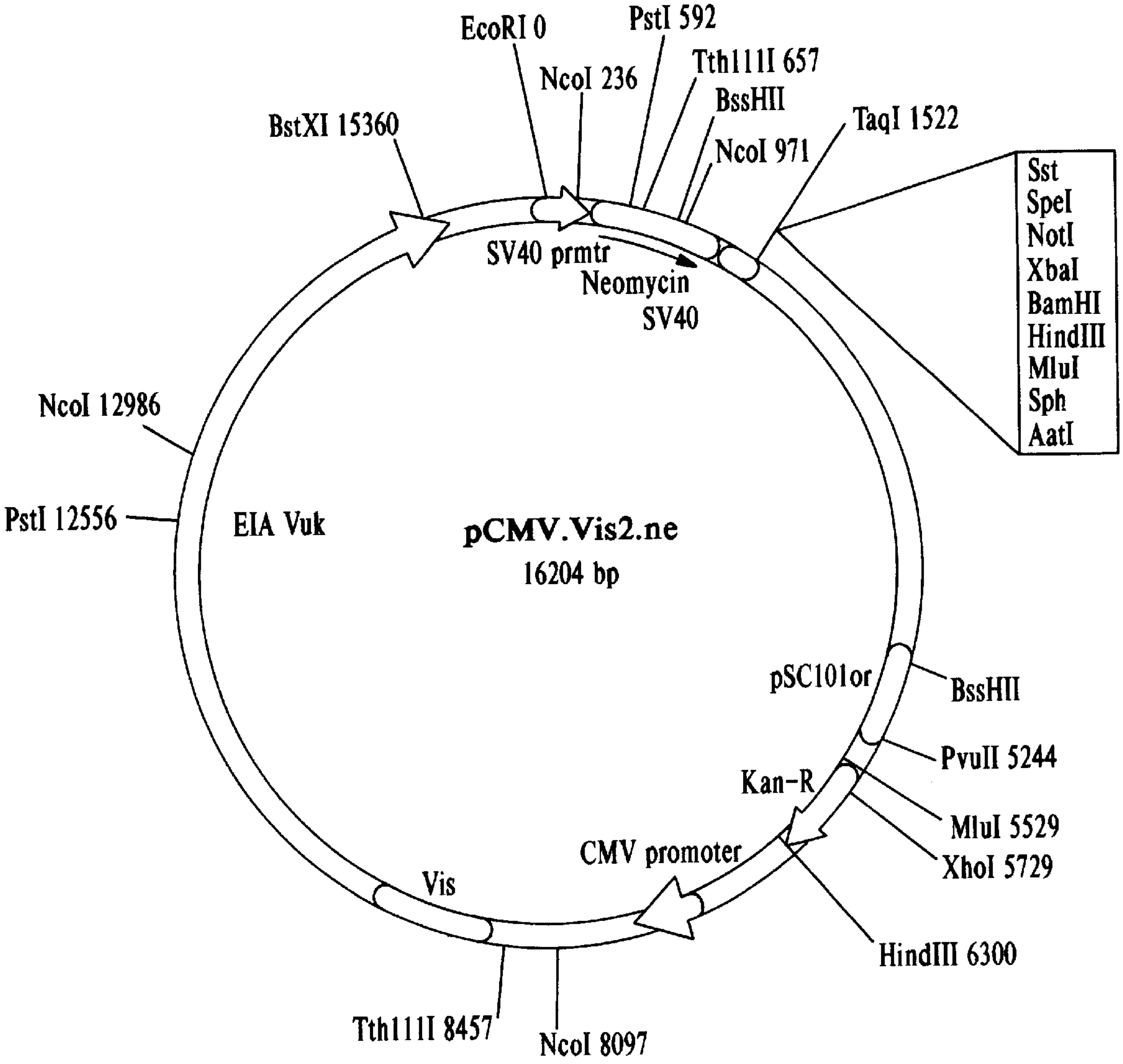
FIG. 6 is a Circular map of the final $pCMVEIAV_{UK}$.Vis2.neo Proviral Construct.

Construction of the p26 Deletion Mutant Proviral Clone designated as pCMV.ΔCA.neo: In order to determine whether deletion of all or part of the CA gene was possible, it was decided to delete the entire p26 gene from EIAV. The molecular clone $EIAV_{UK}$ as described by Cook et al. Journal of Virology 72(2): 1383–1393, 1998 which is incorporated herein by reference, was used for derivation of the proviral clone. FIG. 2 displays a circular map of the $EIAV_{UK}$ molecular clone. FIG. 3*a* displays a linear schematic in order to demonstrate the methods used for the constructs described in this example. FIG. 6 shows the specific sequence of the CA gene and the amino acid sequence of p26 of the EIA virus that it encodes.

The procedure for the construction of the p26 deletion mutant proviral clone (pCMV.ΔCA.neo) was as follows. First, the CMV promoter was inserted into the 5' LTR region through a process of PCR, ligation, and PCR cloning. Primers CMV3'Blunt (SEQ ID No. 1) and 5'CMVBssH (SEQ ID No. 2) were used to amplify the CMV promoter from the plasmid pRC/CMV (InVitrogen). PCR conditions were set up as follows in thin-walled 0.5 ml PCR tubes (PGC Scientific): 40.6 μl $dH_2O$, 5 μl cloned Pfu DNA Polymerase 10× reaction buffer, 0.8 μl 25 mM Deoxy-A,C,G,T (nucleotide) tri-phosphate (dNTP) mixture, 2.5 μl each primer (100 ng/μl), 1 μl template DNA (10 ng/μl) 2.0 μl cloned Pfu DNA Polymerase (2.5 U/μl-Stratagene). Amplification was performed in a Hybaid thermocycler and consisted of 30 cycles of: 94° C.-20 seconds, 60° C.-20 seconds, 72° C.-1 minute. Primers LTRBlunt5' (SEQ ID No. 3) and MA3'Tth (SEQ ID No. 4) were used to amplify a region of the $EIAV_{UK}$ clone encompassing the portion of the genome including the final 31 base pairs of the terminal redundancy region (R region) through the MA open reading frame in similar reaction conditions. The two PCR products (50 $\mu l$) were gel purified on a 0.8% agarose gel with GeneClean (Bio101). The two purified PCR products were set up in individual kinase reactions as follows: 5 $\mu l$ DNA, 2 $\mu l$ ATP, 2 $\mu l$ 10× Protein Kinase buffer (New England Biolabs), 10 $\mu l$ $dH_2O$, and 1 $\mu l$ Protein Kinase. The reaction product was incubated a 37° C. 2 hours. The resulting kinased products were purified through chloroform extraction and ethanol precipitated. The resultant products (3 $\mu l$) were ligated together overnight (16° C.) at their individual blunt ends with T4 ligase (New England Biolabs) in the following reaction mixture: 1 $\mu l$ 10× T4 ligase buffer, 2 $\mu l$ $dH_2O$, and 1 $\mu l$ T4 ligase. A second round of PCR using the primers CMV5'BssH (SEQ ID 2) and MA3'Tth (SEQ ID 4) amplified the final product to be cloned into the $EIAV_{UK}$ clone. The reaction conditions were as stated above using 1 $\mu l$ of the ligation reaction. This final PCR product (50 $\mu l$) was gel purified again on a 0.8% agarose gel. The purified PCR product was digested with the restriction enzymes BssHII and Tth111l in the following manner: 17 $\mu l$ PCR product, 2 $\mu l$ BssHII 10× buffer(NEB), and 2 $\mu l$ BssHII (NEB), incubated at 50° C. for 2 hours, chloroform extracted and ethanol precipitated. The digestion was completed as follows: 16 $\mu l$ DNA (BssHII digested), 2 $\mu l$ 10× reaction buffer #4 (NEB), 2 $\mu l$ Tth111l, incubated at 65° C. for 3 hours. The $EIAV_{UK}$ clone (500 ng) was partially digested with MluI (New England Biolabs). This was conducted through incubation at 37° C. for 5 minutes in the following reaction mixture: 1 $\mu l$ 10× # reaction buffer, 1 $\mu l$ of restriction enzyme, 2 $\mu l$ of $dH_2O$ and immediate submersion on ice followed by gel purification. The appropriate size band was then completely digested with Tth111l in a reaction mixture consisting of 1 $\mu l$ 10× #4 reaction buffer (NEB), 1 $\mu l$ of restriction enzyme and 2 $\mu l$ of $dH_2O$. The resulting fragment was gel purified on a 0.8% agarose gel. The promoter fragment (3 $\mu l$) was ligated into the $EIAV_{UK}$ clone (3 $\mu l$) with T4 ligase in a mixture of 1 $\mu l$ 10× T4 ligase buffer, 2 $\mu l$ $dH_2O$, and 1 $\mu l$ T4 ligase. The resulting ligation product (4 $\mu l$) was transformed into competent DH5α bacterial cells (100 $\mu l$). The transformation procedure consisted of: incubation on ice for 30 minutes, heat shock at 42° C. for 45 seconds, incubation on ice for 2 minutes, addition of 900 $\mu l$ SOC borth (a media supplement containing 20% bacto-tryptone, 5% bacto-yeast, 0.5% NaCl, 2.5 mM KCl, 10 mM magnesium chloride and 20 mM glucose), incubation at 37° C. for 1 hour, and 200 $\mu l$ plated on LBAmp plates. Clones were sequenced to verify correct promoter arrangement as schematically represented in FIG. 3*b*

The PCR, ligation, PCR method of cloning was used to delete the Capsid Antigen (CA) sequence. Primers gag441 (SEQ ID No. 5) and MAT (SEQ ID No. 6) were used to amplify a 398 bp region of the molecularly-modified EIAV designated as $CMVEIAV_{UK}$ genome upstream of the CA open reading frame. PCR conditions were set up as follows in PGC Scientific thin-walled 0.5 ml PCR tubes: 40.6 $\mu l$ $dH_2O$, 5 $\mu l$ cloned Pfu DNA Polymerase 10× reaction buffer, 0.8 $\mu l$ 25 mM dNTP mixture, 2.5 $\mu l$ each primer (100 ng/$\mu l$), 1 $\mu l$ template DNA (10 ng/$\mu l$) 2.0 $\mu l$ cloned Pfu DNA Polymerase (2.5 U/$\mu l$-Stratagene). Amplification was performed in a Hybaid thermocycler. Primers p9f5' (SEQ ID No. 7) and p9f3' (SEQ ID No. 8) were used to amplify a 357 bp region of the $CMVEIAV_{UK}$ genome downstream of the CA encoding region in a similar reaction mixture. These two PCR products (50 $\mu l$) were gel purified on a 0.8% agarose gel with GeneClean (Bio 101). The two purified PCR products (3 $\mu l$) were ligated together overnight (16° C.) with T4 ligase (New England Biolabs) in the following reaction mixture: 1 $\mu l$ 10× T4 ligase buffer, 2 $\mu l$ $dH_2O$, and 1 $\mu l$ T4 ligase. A final round of PCR was performed using the gag441 primer (SEQ ID 5) and p9f3' primer (SEQ ID 8). The ligated sequence, when in the correct orientation would yield a PCR product of approximately 755 bp. This deletes the CA open reading frame from base pairs 846–1550 (EIAV base pair correlation, not plasmid). The PCR product was gel purified on a 0.8% agarose gel with GeneClean. The purified fragment was digested with Tth111l and BsrGI in the following manner: 15 $\mu l$ PCR product, 2 $\mu l$ BSA, 2 $\mu l$ 10× buffer #2 (NEB), and 2 $\mu l$ BsrGI (NEB), incubated at 37° C. for 3 hours, chloroform extracted and ethanol precipitated. The digestion was completed as follows: 16 $\mu l$ DNA(BsrGI digested), 2 $\mu l$ 10× reaction buffer #4 (NEB), 2 $\mu l$ Tth111l, incubated at 65° C. for 3 hours, and gel purified in the same manner previously mentioned. The $CMVEIAV_{UK}$ clone was digested with the same restriction enzymes and gel purified in a similar format. The two fragments (3 $\mu l$ each) were ligated together with T4 ligase in a mixture of 1 $\mu l$ 10× T4 ligase buffer, 2 $\mu l$ $dH_2O$, and 1 $\mu l$ T4 ligase, and transformed into competent DH5α bacterial cells (100 $\mu l$). The transformation procedure consisted of: incubation on ice for 30 minutes, heat shock at 42° C. for 45 seconds, incubation on ice for 2 minutes, addition of 900 $\mu l$ SOC broth, incubation at 37° C. for 1 hour, and 200 $\mu l$ plated on LBAmp plates. Individual clones were screened for insert. Clones were sequenced to verify that the CA region had indeed been deleted as schematically diagrammed in FIG. 3*c*. The symbol Δ identifies the deletion.

The original proviral DNA carried an ampicillin resistance marker ($Amp^r$). Because this would not be the ideal marker for a vaccine used in mammals, it was replaced with a Kanamycin resistant marker ($Kan^r$) using the following procedure. The proviral DNA was subcloned into a kanamycin-resistant vector designated as pLG339/SPORT (Cunningham et al. Gene, 124: 93–98, 1993). The vector was digested with the restriction enzymes MIul and EcoRI (New England Biolabs). The proviral clones were also digested fully with EcoRI and partially digested with MIul. The plasmids (500 ng) were each partially digested individually through incubation at 37° C. for 5 minutes in the following reaction mixture: 2 $\mu l$ 10× #1 reaction buffer, 1 $\mu l$ of restriction enzyme (MIul), 12 $\mu l$ of $dH_2O$ and immediate submersion on ice followed by gel purification. The appropriate size band was then completely digested with EcoRI in a reaction mixture consisting of 1 $\mu l$ 10× #2 reaction buffer, 1 $\mu l$ of restriction enzyme and 2 $\mu l$ of $dH_2O$. The desired fragments were gel purified on a 0.8% agarose gel with GeneClean. The proviral DNA (4 $\mu l$) and vector (2 $\mu l$) were ligated together overnight (16° C.) with T4 ligase (New England Biolabs) in the following reaction mixture: 1 $\mu l$ 10× T4 ligase buffer, 2 $\mu l$ $dH_2O$, and 1 $\mu l$ T4 ligase. The ligation product (4 $\mu l$) was transformed into competent DH5α bacterial cells (100 $\mu l$). The transformation procedure consisted of: incubation on ice for 30 minutes, heat shock at 42° C. for 45 seconds, incubation on ice for 2 minutes, addition of 900 $\mu l$ SOC broth, incubation at 37° C. for 1 hour, and 200 $\mu l$ plated on LBKan plates. Individual clones were screened for insert into the proper MIul site. FIG. 3*d* shows a schematic representation of this construct demonstrating the Amp resistance marker being replace by the Kan resistance marker.

Figure 4:
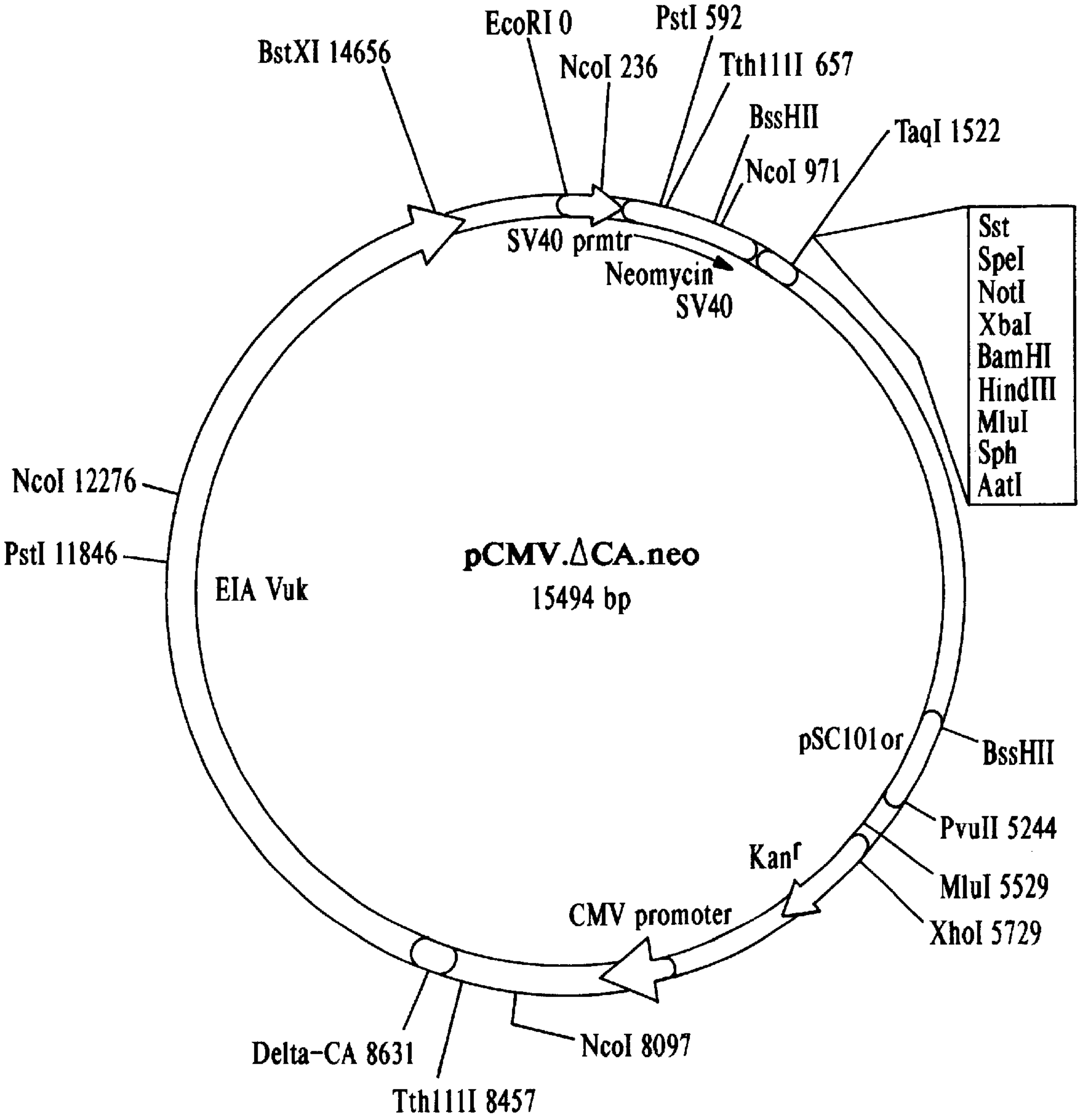
FIG. 4 is a circular map of the p26-deleted Proviral Clone pCMV.ΔCA.neo.

A neomycin resistance marker ($Neo^r$) was added in order to allow selection of clones in eukaryotic cells. The neomycin resistance marker was excised from the commercial vector pRC/CMV (InVitrogen) using the restriction enzymes EcoRI and XhoI (New England Biolabs). The area excised from the pRC/CMV encompassed the entire neomycin open reading frame as well as the SV40 promoter, origin of replication, and SV40 poly A recognition sequence. The digestion was executed at 37° C. in a reaction mixture which consisted of 500 ng pRC/CMV plasmid DNA, 2 μl 10× #2 reaction buffer, 2 μl BSA, 2 μl $dH_2O$, and 1 μl each of the restriction enzymes. The resulting kanamycin-resistant proviral clone was digested with the restriction enzymes EcoRI and SalI (GIBCO BRL). SalI digested ends can ligate into XhoI digested ends. The digestion was carried out in the following reaction mixture: 1 μl proviral DNA, 2 μl 10× REACT 6 buffer, 2 μl BSA, 2 μl $H_2O$ and 1 μl each restriction enzyme. The digested neomycin fragment and proviral clone were gel purified on a 0.8% agarose gel with GeneClean, and ligated together at 16° C. overnight with T4 ligase in the following reaction mixture: 4 μl purified proviral DNA, 3 μl purified neomycin insert DNA, 1.5 μl 10× T4 ligase buffer, 5.5 μl $dH_2O$ and 1 μl T4 ligase. The ligated DNA (6 μl) was transformed into competent DH5α bacterial cells (100 μl). The transformation procedure consisted of: incubation on ice for 30 minutes, heat shock at 42° C. for 45 seconds, incubation on ice for 2 minutes, addition of 900 μl SOC broth, incubation at 37° C. for 1 hour, and 200 μl plated on LBKan plates. Individual clones were screened for insert. A schematic representation of the p26 deleted Proviral Clone pCMV.ΔCA.neo is shown in FIG. 3*e* with a circular map shown in FIG. 4.

EXAMPLE 2

Construction of an EIAV wherein a gene from a non-EIAVorganism is inserted into the deleted p26 region (designated as pCMV.Vis2.neo): In order to substitute a foreign gene into the Capsid Antigen region (CA) of the gag gene and perhaps, to produce a replicating Proviral Clone with a p26 deletion, it was decided to insert the p30 gene from a Visna virus, a lentivirus (non-EIAV organism) which does not produce a positive response on the Coggins Test. If the p30 could be adapted to replace the mechanism for p26 of the EIAV, then a replicating proviral clone could be produced.

As in EXAMPLE 1, the backbone for the construction of the Proviral Clone with the p30 of Visna inserted into the deleted p26 region was $EIAV_{UK}$ (Cook et al., ibid). A schematic diagram of this starting construct is shown in FIG. 5*a*.

The procedure for preparation of this EIAV construct was as follows: The CMV promoter was inserted into the 5' LTR region of $EIAV_{UK}$ through a process of PCR, ligation, PCR cloning as referenced previously. Primers CMV3'Blunt (SEQ ID No.1) and 5'CMVBssH (SEQ ID No.2) were used to amplify the CMV promoter from the plasmid pRC/CMV (InVitrogen). PCR conditions were set up as follows in PGC thin-walled 0.5 ml PCR tubes: 40.6 μl $dH_2O$, 5 μl cloned Pfu DNA Polymerase 10× reaction buffer, 0.8 μl 25 mM dNTP mixture, 2.5 μl each primer (100 ng/μl), 1 μl template DNA (10 ng/μl) 2.0 μl cloned Pfu DNA Polymerase (2.5 U/μl-Stratagene). Amplification was performed in a Hybaid thermocycler and consisted of 30 cycles of: 94° C.-20 seconds, 60° C.-20 seconds, 72° C.-1 minute. Primers LTRBlunt5' (SEQ ID No. 3) and MA3'Tth (SEQ ID NO. 4) were used to amplify a region of the $EIAV_{UK}$ clone encompassing the portion of the genome including partial R region through the matrix open reading frame in similar reaction conditions. The PCR products (50 μl) were gel purified on a 0.8% agarose gel with GeneClean (Bio 101). The two purified PCR products were set up in individual kinase reactions as follows: 5 μl DNA, 2 μl ATP, 2 μl 10× Protein Kinase buffer (New England Biolabs), 10 μl $dH_2O$, and 1 μl Protein Kinase. The reaction was incubated a 37° C. 2 hours. The kinased products were purified through chloroform extraction and ethanol precipitated. The resultant products (3 μl) were ligated together overnight (16° C.) at their individual blunt ends with T4 ligase (New England Biolabs) in the following reaction mixture: 1 μl 10× T4 ligase buffer, 2 μl $dH_2O$, and 1 μl T4 ligase. A second round of PCR using the primers CMV5'BssH (SEQ ID No. 2) and MA3'Tth (SEQ ID No. 4) amplified the final product to be cloned into the $EIAV_{UK}$ clone. The reaction conditions were as stated above using 1 μl of the ligation reaction. This final PCR product (50 μl) was gel purified again on a 0.8% agarose gel. The purified PCR product was digested with the restriction enzymes BssHll and Tth1111 in the following manner: 17 μl PCR product, 2 μl BssHll 10× buffer(NEB), and 2 μl BssHll (NEB), incubated at 50° C. for 2 hours, chloroform extracted and ethanol precipitated. The digestion was completed as follows: 16 μl DNA (BssHll digested), 2 μl 10× reaction buffer #4 (NEB), 2 μl Tth1111, incubated at 65° C. for 3 hours. The $EIAV_{UK}$ clone (500 ng) was partially digested with MIul (New England Biolabs). This was conducted through incubation at 37° C. for 5 minutes in the following reaction mixture: 1 μl 10× # reaction buffer, 1 μl of restriction enzyme, 2 μl of $dH_2O$ and immediate submersion on ice followed by gel purification. The appropriate size band was then completely digested with Tth1111 in a reaction mixture consisting of 1 μl 10× # reaction buffer, 1 μl of restriction enzyme and 2 μl of $dH_2O$. The fragment was gel purified on a 0.8% agarose gel. The promoter (3 μl) was ligated into the $EIAV_{UK}$ clone (3 μl) with T4 ligase in a mixture of 1 μl 10× T4 ligase buffer, 2 μl $dH_2O$, and 1 μl T4 ligase. The ligation product (4 μl) was transformed into competent DH5α bacterial cells (100 μl). The transformation procedure consisted of: incubation on ice for 30 minutes, heat shock at 42° C. for 45 seconds, incubation on ice for 2 minutes, addition of 900 μl SOC broth, incubation at 37° C. for 1 hour, and 200 μl plated on LBAmp plates. Clones were sequenced to verify correct promoter arrangement. FIG. 5*b* is a schematic representation of the $EIAV_{UK}$ clone with the CMV promoter insert ($CMVEIAV_{UK}$).

The source of the Visna p30 capsid sequence was the pVisna clone puc9-4.9V2 (Braun, M J et al, Journal of Virology, 61(12): 4046–4054, 1987). The Visna p30 (7 μl containing 1 μg) was excised out of the clone using the restriction enzymes Apal and Tth1111 in the following reaction: 4 μl $dH_2O$, 1.5 μl BSA, 1.5 μl 10× #4 reaction buffer (NEB), 0.5 μl Apal and Tth1111 (NEB), incubated at 65° C. for 2 hours; 0.5 μl more of Apal added to the reaction mixture and incubated at room temperature (25° C.) overnight. The desired fragment was gel purified in a 0.8% agarose gel with GeneClean. The $CMVEIAV_{UK}$ clone (5 μl containing 1 μg) was digested with Blpl (NEB enzyme for Bpu1102l) and Tth1111 (NEB) in the following reaction mixture: 1.5 μl 10× buffer #4 (NEB), and 1 μl BsrGI (NEB), 7.5 μl $dH_2O$, incubated at 37° C. for 3 hours, chloroform extracted and ethanol precipitated. The digestion was completed as follows: 15 μl DNA(Blpl digested), 2 μl 10× reaction buffer #4 (NEB), 1 μl Tth1111, 2 μl $dH_2O$, incubated at 65° C. for 3 hours. The digested proviral DNA was gel purified on a 0.8% agarose gel with GeneClean. The two fragments were ligated with T4 ligase in the following mixture: DNA fragments (3 μl each) were ligated together with T4 ligase in a mixture of 1 μl 10× T4 ligase buffer, 2 μl $dH_2O$, and 1 μl T4 ligase. The ligation product (4 μl) was transformed into competent DH5α bacterial cells (100 μl). The transformation procedure consisted of: incubation on ice for 30 minutes, heat shock at 42° C. for 45 seconds, incubation on ice for 2 minutes, addition of 900 μl SOC broth, incubation at 37° C. for 1 hour, and 200 μl plated on LBAmp plates. Individual clones were screened for insert and sequenced using dideoxy sequencing and an ABI automatic sequencer to verify the entire visna p30 open reading frame was inserted in the proviral clone correctly and in frame. FIG. 5*c* shows a schematic of the $CMVEIAV_{UK}$.vis2.

The proviral DNA was subcloned into a kanamycin-resistant vector designated as pLG339/SPORT (Cunningham et al. Gene, 124: 93–98, 1993), incorporated herein by reference. The vector was digested partially with MIul and fully with EcoRI (New England Biolabs). The proviral clones were also digested fully with EcoRI and partially digested with MIul. The plasmids (500 ng) were each partially digested individually through incubation at 37° C. for 5 minutes in the following reaction mixture: 2 μl 10× #2 reaction buffer, 1 μl of restriction enzyme, 12 μl of $dH_2O$ and immediate submersion on ice followed by gel purification. The appropriate size band was then completely digested with EcoRI in a reaction mixture consisting of 1 μl 10× #2 reaction buffer, 1 μl of restriction enzyme and 2 μl of $dH_2O$. The desired fragments were gel purified on a 0.8% agarose gel with GeneClean. The proviral DNA (4 μl) and vector (2 l) were ligated together overnight (16° C.) with T4 ligase (New England Biolabs) in the following reaction mixture: 1 μl 10× T4 ligase buffer, 2 μl $dH_2O$, and 1 μl T4 ligase. The ligation product (4 μl) was transformed into competent DH5α bacterial cells (100 μl). The transformation procedure consisted of: incubation on ice for 30 minutes, heat shock at 42° C. for 45 seconds, incubation on ice for 2 minutes, addition of 900 μl SOC broth, incubation at 37° C. for 1 hour, and 200 μl plated on LBKan plates. Individual clones were screened for insert into the proper MIul site. FIG. 5*d* shows a schematic of the proviral clone containing the kanamycin resistance marker.

In order to make the EIAV proviral construct more commercially-acceptable, the kanamycin resistance marker was replaced with a neomycin resistance marker. The neomycin resistance marker was excised from the commercial vector pRC/CMV (InVitrogen) using the restriction enzymes EcoRI and XhoI. This encompassed the entire neomycin open reading frame as well as the SV40 promoter (SEQ ID No. 9), origin of replication (SEQ ID. No. 10), and SV40 poly A recognition sequence (SEQ ID. No. 11). The digestion was executed at 37° C. in a reaction mixture that consisted of 500 ng pRC/CMV plasmid DNA, 2 μl 10× #2 reaction buffer, 2 μl BSA, 2 μl $dH_2O$, and 1 μl each of the restriction enzymes. The new kanamycin-resistant proviral clone was digested with the restriction enzymes EcoRI and SalI (GIBCO BRL). SalI digested ends can ligate into XhoI digested ends. The digestion was carried out in the following reaction mixture: 1 μg proviral DNA, 2 μl 10× REACT 6 buffer, 2 μl BSA, 2 μl H2O and 1 μl each restriction enzyme. The digested neomycin fragment and proviral clone were gel purified on a 0.8% agarose gel with GeneClean, and ligated together at 16° C. overnight with T4 ligase in the following reaction mixture: 4 μl purified proviral DNA, 3 μl purified neomycin insert DNA, 1.5 μl 10× T4 ligase buffer, 5.5 μl $dH_2O$ and 1 μl T4 ligase. The ligated DNA (6 μl) was transformed into competent DH5α bacterial cells (100 μl). The transformation procedure consisted of: incubation on ice for 30 minutes, heat shock at 42° C. for 45 seconds, incubation on ice for 2 minutes, addition of 900 μl SOC broth, incubation at 37° C. for 1 hour, and 200 μl plated on LBKan plates. Individual clones were screened for insert. FIG. 5*e* shows a schematic drawing of the final $pCMVEIAV_{UK}$.Vis2.neo proviral construct (hereinafter designated pCMV.Vis2.neo) and FIG. 6 shows the final circular map of this construct.

The pCMV.Vis2.neo proviral construct was tested for its ability to replicate in vitro by using the standard replication assay as described in EXAMPLE 1. As with the Proviral Clone pCMV.ΔCA.neo, this pCMV.Vis2.neo proviral construct did not replicate in vitro and would not be expected to replicate in vivo. It was therefore decided to develop a transfected cell line (persistently-infected cell line).

EXAMPLE 3

Transfection & Selection of Cell Lines: Transfection of an Equine Dermal Cell Line The p26-deleted Proviral Clone pCMV.ΔCA.neo and proviral construct pCMV.Vis2.neo were used to evaluate their ability to transfect cells in a manner similar to the wild-type $EIAV_{UK}$. The procedure used was as follows.

One microgram of proviral clone or proviral construct DNA was used to transfect an Equine Dermal (ED) cell line (ATCC CRL 6288). The ED cell line was grown in 6 well tissue culture plates seeded with between 2 and $4\times10^5$ ED cells per well in 2 mL of the complete growth Minimum Essential Media with Earles salts (EMEM) plus 10% fetal calf serum, 100 units/mL of penicillin, 100 μg/mL of streptomycin (Gibco BRL 15140-122) and 2 mm L-glutamine (Gibco BRL 25030-081). The plates were incubated at 37° C. in a $CO_2$ incubator approximately 16 to 24 hours until the cells are between 50 and 80% confluent. For each transfection, 1 μg of DNA was diluted into 100 μL of OPTI-MEM I Reduced Serum Medium (Gibco BRL 18324-012) and 10 μL of Lipofectamine reagent (Gibco BRL 18324-012) was added to 100 μL of OPTI-MEM I Reduced Serum Medium (OPTI-MEM RSM). The two solutions were mixed gently and incubated at room temperature for 30 minutes to allow the DNA-liposome complexes to form. During this time, the ED cell cultures were rinsed once with 2 mL of OPTIMEM I RSM (GIBCO-BRL). For each transfection, 0.8 mL of OPTIMEM I RSM was added to the tube containing the DNA-liposome complexes, the tube was mixed gently and the contents were overlayed onto the rinsed cells. No antibiotics were added during transfection. The DNA-liposome/tissue cultures were incubated for 5 hours at 37° C. in a $CO_2$ incubator. Following incubation, 1 mL of complete growth MEM containing twice the normal concentration of serum was added to the cell culture without removing the transfection mixture. Twenty four hours following the start of transfection the medium was replaced with fresh complete growth medium (EMEM). Starting at 48 to 72 hours post transfection, aliquots of the tissue culture supernatants were taken at periodic intervals and analyzed by using a standard reverse transcriptase (RT) assay as a measure of virus production. Supernatants resulting in RT activity were titrated in an infectivity assay based on cell-ELISA readings as described by Lichtenstein et al, 1995. Neither the Proviral Clone pCMV.ΔCA.neo nor the proviral construct pCMV.Vis2.neo replicated in tissue culture. The RT levels were less than or equal to those of the negative control in tissue culture cells normally capable of being infected with EIAV, that were exposed to the culture medium from the transfected cells. Therefore, it was determined that the deletion of p26 produced a defective virus particle, unable to replicate in vitro or in vivo. In order to obtain particles for large-scale vaccine production, it was decided to produce a persistently-infected cell line with the Proviral Clone pCMV.ΔCA.neo and proviral construct pCMV.Vis2.neo.

Transfection of COS Cells

Virus particles were produced using Proviral Clone pCMV.ΔCA.neo and the proviral construct pCMV.Vis2.neo transfected in the monkey cell line COS-1 (ATCC_CRL 1650). Cells were plated at approximately 50% confluency into 60 mm plates (Falcon) 24 hours prior to transfection. Approximately 1 μg of proviral clone DNA (pCMV.ΔCA.neo or pCMV.Vis2.neo ) was transfected into the cells using DEAE Dextran methodology. Briefly, a 50 mg/ml solution of DEAE dextran was diluted 1:50 (1 mg/ml final concentration) in Tris-buffered saline (TBS) with DNA and added to the cells in serum-free media (DMEM). The DNA solution was incubated on the cells for 1 hour at 37° C. in the presence of 5% $CO_2$ with rocking every 15 minutes. Regular growth medium was replaced at this point. Forty-eight hours post-transfection the supernatants were assayed for RT activity. The RT activity was detected in cell-free supernatant samples using the micro reverse transcriptase assay (Lichtenstein et al., ibid). Protein content was detected using a Western Blot Anlaysis procedure. For this procedure, virus particles were pelleted from 10 mls of cell-free supernatant over a 20% glycerol cushion in an ultracentrifuge (Beckman SW41Ti rotor) at 50,000×g for 45 min. Pellets were lysed in 100 l of lysis solution containing 10 mM NaCl, 1% Deoxycholic acid (DOC), 0.1% Sodium Dodecyl Sulfate (SDS), 25 mM Tris-HCl and 1% TritonX-100 and transferred to 1.5 ml eppendorf tubes. After lysis, the samples were boiled in 20 μl of 6× SDS gel loading buffer and loaded onto a 12% SDS-polyacrylamide gel. Gradient purified $EIAV_{PV}$ (1 μg) was also loaded onto the gel to serve as a marker for viral proteins. Electrophoresis was carried out at approximately 10 mA overnight with cooling. Proteins were transferred onto Millipore membranes using BioRad's protein transfer cell system in a buffer containing 25 mM Tris, 192 mM glycine, 20% methanol and 0.05% SDS. Transfer was completed after 3 hours at 400 mA with cooling. EIAV proteins were detected using monoclonal antibodies. Prior to antibody incubation the blot was blocked in 5% blotto (5% drymilk, 5% FBS and 0.25% Tween-20 in 1×PBS) for 1 hour at room temperature. Mouse monoclonal α-gp90 and α-p26 were used together in 5% blotto for 1 hour at room temperature. Secondary antibody α-mouse 1 gG conjugated with horse-radish-peroxidase (Sigma lot #115H8995) was incubated at room temperature for one hour. The blot was washed for 3–5 minute periods in 1×PBS/0.025% Tween-20 between primary and secondary antibody incubations. A one minute incubation at room temperature of the chemi-illuminescent substrate SuperSignal (Pierce lot #AE40027) followed the final wash after the secondary antibody incubation. Exposure of the blot to film demonstrated that both gp90 and p26 were detectable in the EIAVPV positive control; but only gp90 was detectable in the proviral clone pCMV.ΔCA.neo and the proviral construct pCMV.Vis2.neo. Production of the virus particles was observed through both RT activity and by Western Blot analysis.

Stable Transfections in CHO, C-33A & ED-MCS Cell Lines

Figure 10A:
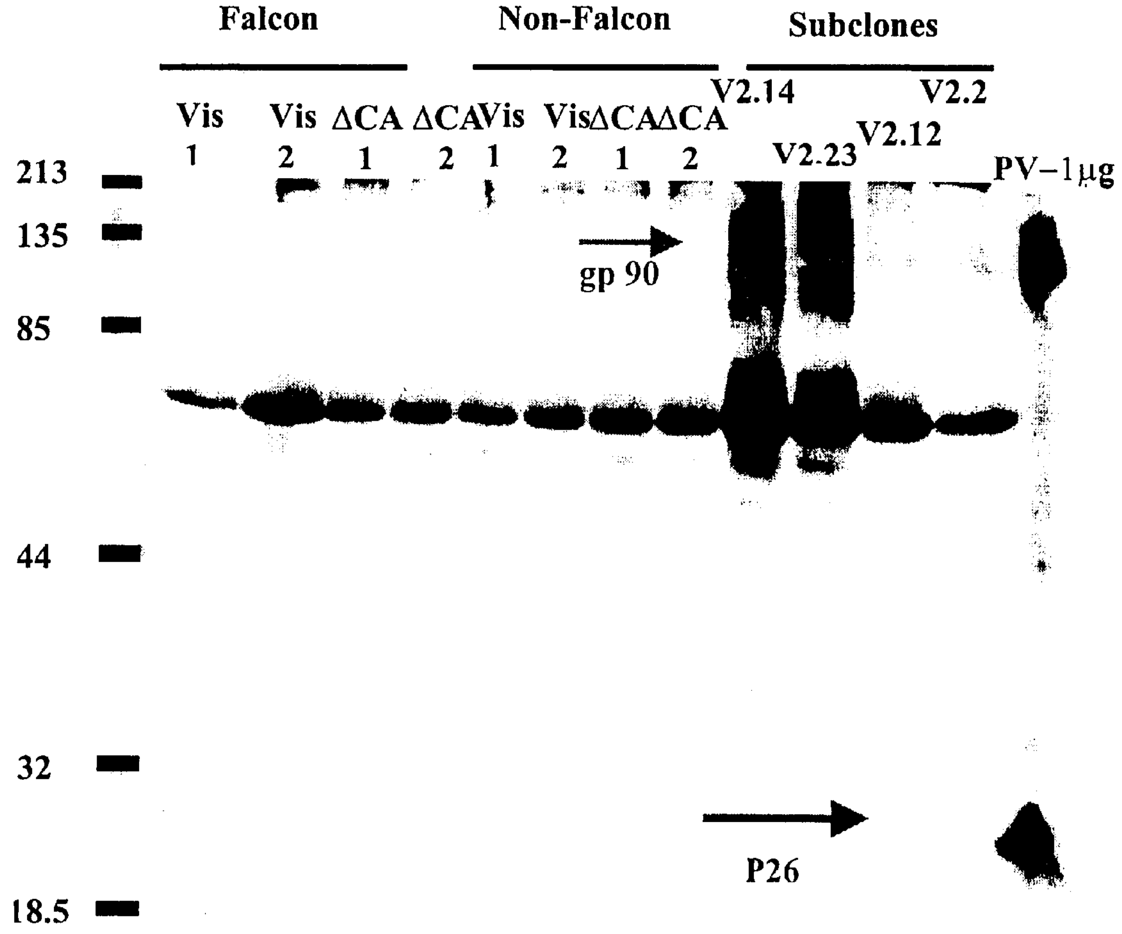
FIG. 10*a* is a Western Blot of p26-deleted clones, Visna chimeric clones & subclones of EIAV using gp90 & p26 monoclonal antibodies as the detector.
Figure 10B:
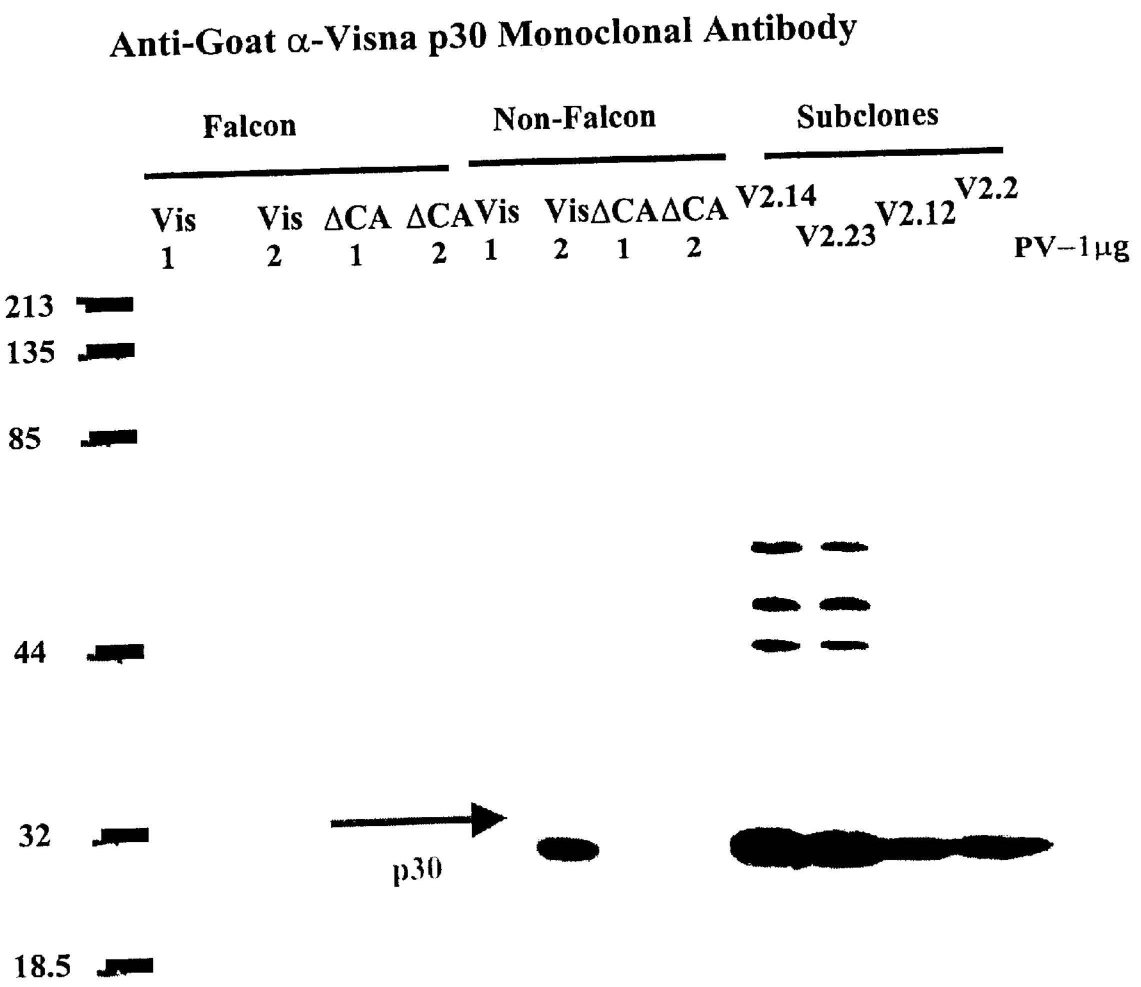
FIG. 10*b* is a Western Blot of several p26-deleted clones, Visna chimeric clones & subclones of EIAV using p30 monoclonal antibody as the detector.

Stable production of virus particles was attempted in three cell lines; a human cell line C-33A (ATCC HTB-31), a chinese hamster ovary cell , CHO (ATCC CRL-9618), and an equine cell line ED-MCS. Transfections were all done in duplicate. Cells were consistently maintained in an incubator at 37° C. with 5%$CO_2$. Cell lines were seeded onto 10 mm plates manufactured by Sarstedt and Falcon 24 hours prior to transfection at the following densities: CHO & C-33A $1\times10^6$ cells/plate, ED-MCS $3.5\times10^5$ cells/plate. Proviral clones, pCMV.Vis2.neo and pCMV.ΔCA.neo (20 μg/plate) were transfected into the cells using 55 μl of the reagent GenePORTER™ (Gene Therapy Systems) in serum-free DMEM (Gibco). Manufacturers' instruct ions were followed. Twenty-four hours post-transfection media was changed from transfection media to selection media (DMEM) which contained 800 μg/ml G-418 (Geneticin, Gibco BRL) and 10% FBS (Hyclone). A plate that was not transfected was carried as a control for selection in the same media. Once the control plate had no viable cells present and the selected plates displayed colony formation, cells were passed into T75 flasks (Falcon) as bulk cultures. The level of G-418 in the ED-MCS cells was increased to 1000 μg/ml due to rapid growth. Supernatants were analyzed throughout the selection period for RT activity and at individual points assayed for protein content through Western blot analysis. RT activity initially indicated highest production in the human and mouse cell lines. The equine dermal cell line proved to develop the most stable construct during long-term production, producing continuously the highest levels out to post-selection day 150. This experiment proved that tissue culture cells can be transfected by the p26-deleted clone as well as by the chimera wherein a foreign gene from a Visna virus (p30) was inserted into the p26 region. Reverse trascriptase activity from these trasnfected cells reached levels as high as 10,000 CPM/10 μl of tissue culture fluid. This is equivalent to RT activity produced by wild-type EIAV when transfected into tissue culture. Western Blot analysis was conducted as described previously except that a second western blot was done in the same format as before, re-probing the membrane with goat α-Visna p30 to detect the Visna chimera proteins. Secondary antibody was α-goat IgG whole molecule-HRP (Sigma lot#117H4831). The Visna p30 protein was detected in the Visna chimeric proviral construct pCMV.Vis2.neo (See FIG. 10*b*).

Western Blot Analysis

Virus particles were pelleted from 10 mls of cell-free supernatant over a 20% glycerol cushion in the ultracentrifuge SW41Ti rotor (Beckman). Pellets were lysed in 100 μl of lysis solution containing 10 mM sodium chloride (NaCl), 1% DOC, 0.1% Sodium Dodecyl Sulafte (SDS), 25 mM Tris-HCl and 1% TritonX-100 and transferred to 1.5 ml eppendorf tubes. After lysis, the samples were boiled in 20 μl of 6× SDS buffer gel loading buffer and loaded onto a 12% SDS-polyacrylamide gel. One microgram of gradient purified pony virus $EIAV_{PV}$ was also loaded onto the gel to serve as a marker for viral proteins. Electrophoresis was carried out at approximately 10 mA overnight with cooling. Proteins were transferred onto Millipore membranes using BioRad's protein transfer cell system in a buffer containing 25 mM Tris, 192 mM glycine, 20% methanol and 0.05% SDS. Transfer was completed after 3 hours at 400 mA with cooling. EIAV proteins were detected using monoclonal antibodies. Prior to antibody incubation the blot was blocked in 5% blotto (5% drymilk, 5% FBS and 0.25% Tween-20 in 1×PBS) for 1 hour at room temperature. Mouse monoclonal α-gp90 and α-p26 were used together in 5% blotto for 1 hour at room temperature. Secondary antibody α-mouse IgG conjugated with horse-radish-peroxidase (Sigma lot #115H8995) was incubated at room temperature for one hour. The blot was washed for 3–5 minute periods in 1×PBS/0.025% Tween-20 between primary and secondary antibody incubations. A one minute incubation at room temperature of the chemi-illuminescent substrate SuperSignal (Pierce lot #AE40027) followed the final wash after the secondary antibody incubation. Exposure of the blot to film demonstrated that both gp90 and p26 were detectable in the PV positive control; but only gp90 was detectable in the proviral clones (pCMV.Vis2.neo and pCMV.CA.neo), see FIG. 10*a* The membranes were stripped through incubation in Glycine-Cl pH 2.3 buffer (0.05M glycine 0.15M NaCl) for 45 minutes. The membranes were washed in the same wash buffer for 7–5 minute periods and blocked in 5% blotto for 2 hours. The second western was done in the same format as before, re-probing the membrane with goat α-Visna p30 to detect the Visna chimera proteins. Secondary antibody was α-goat IgG whole molecule-HRP (Sigma lot#117H4831). The Visna p30 protein was detected in the Visna chimeric proviral constructs (pCMV.Vis2.neo) see FIG. 10*b*.

The presence of gp90 indicates that these p26-deleted constructs produce the protective antigen. Not only do they lack the ability to produce p26 antibodies in animals but they also cause the animals vaccinated with them to produce antibodies to p30. The presence of p30 in an equine will indicate that the horse has been vaccinated. An assay to detect the presence of this p30 antibody can be developed in order to differentiate horses that are vaccinated with the vaccines of this invention from horses that have not been vaccinated or horses that have been infected with wild-type EIAV. Additionally, a diagnostic that detects all or part of the p30 gene sequence or the p30 protein can be used similarly as a diagnostic tool.

EXAMPLE 4

Subcloning—Single Cell Cloning of the Stable Transfection

Stablely-selected Visna (pCMV.Vis2.neo) transfected ED-MCS cells which had been frozen back at day 40 of selection were thawed at 37° C. and seeded into a T75 flask in normal growth medium (no G-418). Cells were grown at 37° C. with 5% $CO_2$ in G-418-negative medium for 48-hours prior to plating for cloning. Cells were trypsonized from the T75 flasks, counted, and plated onto 100 mm Falcon plates at densities of approximately 100 cells per plate. The cells were selected in medium containing 800 μg/ml G-418. Media was changed approximately every four days and cells were grown in the plates until visible colonies had formed. Independent colonies were trypsonized from the plates separately through the use of cloning cylinders and seeded into separate cells of Falcon 24-well plates. These were also selected in media containing 800 μg/ml G-418. Approximately 7 days post-transfer the cell supernatants were assayed for RT activity. The was conducted as follows:

For each 10 μl sample of cell-free supernatant to be assayed the following is added:

| | |
|---|---|
| $^3$H-TTP (40 Ci/mmol) - dried in speedvac and volume made up with the volume of water below | 1.5 μl |
| 100 mM EGTA | 5.0 μl |
| 10 X Salts (2M Tris-Cl pH 8.0, 2M KCl, 1M $MgCl_2$, 1M DTT, 20% NP-40, DI Water) | 5.0 μl |
| poly(rA).p(dT)$_{12-13}$ (5 units/ml ~ .25 mg/ml) | 2.0 μl |
| millipore water | 38.0 μl |
| | 50.0 μl |

Figure 11:
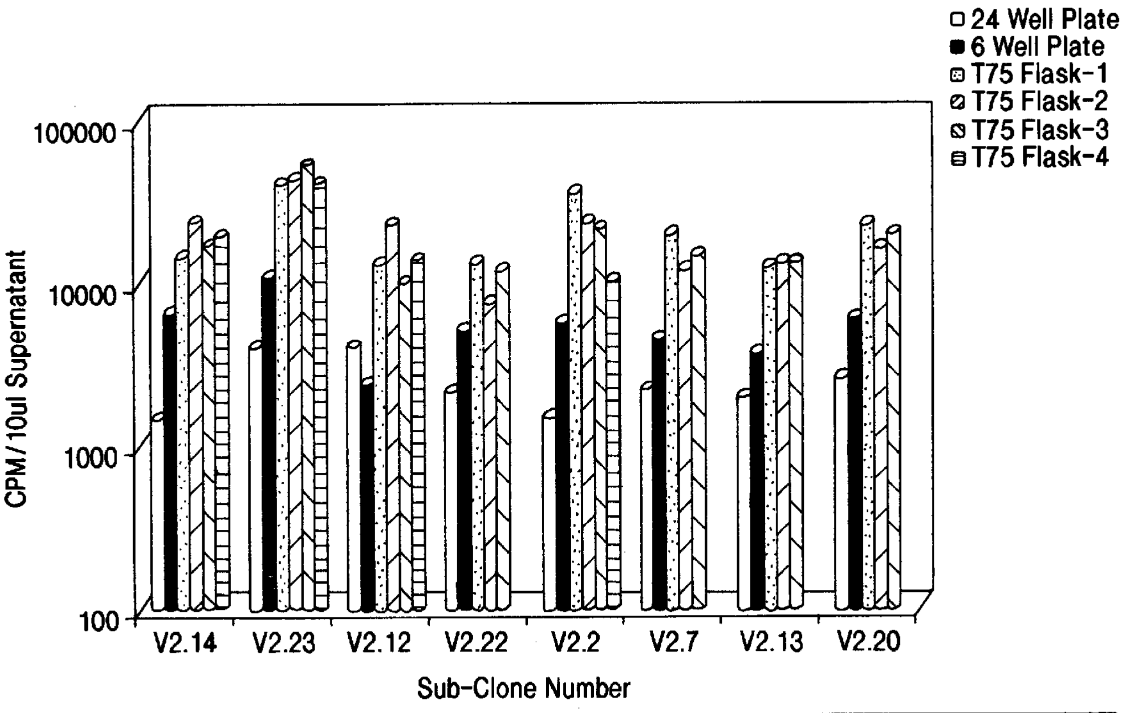
FIG. 11 is a graph demonstrating the Reverse Transcriptase Activity of various subclones of ED cells transfected with pCMVEIAVUK.Vis2neo Proviral Construct.

The mixture of supernatant (sample) and reaction mixture are mixed together and incubated at 37° C. for 1.5 hr–2.0 hr. The total volume is (~60 μl) pipetted onto DEAE coated filter paper and allowed to dry completely. The filters are then washed 3× for 15 minute each in 1× SSC and again allowed to dry completely. The filters are then immersed in scintillation fluid and the incorparated activity measured. As a result of using this RT assay, the 12 "subclones" with the highest RT activity were trypsonized and passaged into 6-well plates (Falcon), still selecting in 800 μg/ml G-418. Supernatants were analyzed for RT activity after 4 days of selection in the 6-well plates. The 8 subclones with the highest RT activity were trypsonized and passaged into T75 flasks (Falcon) still selecting in 800 μg/ml G-418. Supernatants were analyzed for RT activity after 7 days of selection in the flasks. The amount of G-418 was reduced at this passage point to 600 μg/ml. Selection was carried out for 4 more days, RT activity analyzed, and the level of G-418 lowered again to 400 μg/ml. After 7 days of selection another RT assay was performed on the 8 subclones to monitor selection. Following 7 more days of selection, another RT assay was performed. The 4 highest producing cell lines were passaged again, lowering the level of G-418 to 200 μg/ml (the other 4 were frozen back). The highest-producing subclone, F-1V2.23, was producing a high level of RT activity (between 4000 and 50,000 CPM per 10 μl of tissues culture fluid as shown in FIG. 11. This result indicates that the constructs of this invention can be produced in vitro in enough quantity to produce commercial vaccines.

The fact that the constructs of this invention were able to demonstrate the presence of the gp90 protective component and displayed significant EIAV RT activity provides assurance that a vaccine prepared according to this invention would be useful in protecting animals from disease and/or infection from lentiviruses, particularly EIAV. Additionally, it has been demonstrated that said vaccine lacks the ability to stimulate antibodies to p26 and that it would produce antibodies to p30 so that vaccinated animals can be differentiated from infected or non-exposed animals. Most importantly, the insertion of a foreign gene into the EIAV genome such that said foreign gene is expressed indicates the usefulness of this lentivirus as a vector or as a virus construct into which multiple genes could be inserted. Such a multiple gene insertion could provide for an EIAV vaccine that protects from multiple diseases.

Although the invention has been described in detail in the foregoing, for the purpose of illustration it is to be understood that such detail is solely for that purpose and that variations can be made therein by those skilled in the art without departing from the spirit and scope of the invention except as it may be limited by the claim.

I claim:

1. An immunogenic composition that produces protection from Equine Infectious Anemia (EIA) disease comprising a non-replicating Equine Infectious Anemia Virus (EIAV) that lacks the ability to express a Capsid Antigen.

2. The immunogenic composition according to claim 1 wherein the non-replicating EIAV lacks the ability to express p26 antigen.

3. The immunogenic composition according to claim 2 wherein the lack of ability to express p26 antigen results from a non-functional gag gene.

4. The immunogenic composition according to claim 3 wherein the non-functional gag gene results from a deletion in the gag gene.

5. The immunogenic composition according to claim 4 wherein the deletion in the gag gene results from one or more deletions in a gene region selected from the group consisting of a portion of the gag gene, all of the gag gene, a gene regulating expression of the gag gene and an insertion of a stop codon in a gene affecting the expression of the gag gene.

6. The immunogenic composition according to claim 4 wherein the gene-deleted EIAV further lacks the ability to replicate in vitro.

7. An immunogenic composition for effectively and safely immunizing equines from EIA, said immunogenic composition comprising a gene-deleted, non-replicating EIAV wherein said gene-deleted EIAV lacks the ability to express p26 and allows differentiation of vaccinated from wild type exposed equines.

8. The immunogenic composition of claim 7 further comprising an adjuvant.

9. The immunogenic composition of claim 7 wherein the EIAV is inactivated.

10. A method of immunizing mammals against disease produced by an EIAV comprising, administering to said mammals the immunogenic composition of claims 1 or 2.

11. An EIAV immunogenic composition that allows equines to be safely vaccinated and protected from disease and/or infection without converting to a seropositive status on the Coggins Test or any other test which measures p26 antibodies.

* * * * *

SEQUENCE LISTING

<160> NUMBER OF SEQ ID NOS: 11

<210> SEQ ID NO 1
<211> LENGTH: 24
<212> TYPE: DNA
<213> ORGANISM: GIBCO

<400> SEQUENCE: 1
aatttcgata agccagttaa gcag 24

<210> SEQ ID NO 2
<211> LENGTH: 26
<212> TYPE: DNA
<213> ORGANISM: GIBCO

<400> SEQUENCE: 2
ctggcgcgcg atcgacgggc cagata 26

<210> SEQ ID NO 3
<211> LENGTH: 28
<212> TYPE: DNA
<213> ORGANISM: GIBCO

<400> SEQUENCE: 3
ggcctttcta ataaatataa ttctctac 28

<210> SEQ ID NO 4
<211> LENGTH: 27
<212> TYPE: DNA
<213> ORGANISM: GIBCO

<400> SEQUENCE: 4
aggcctctct tccttgtcct gacagcg 27

<210> SEQ ID NO 5
<211> LENGTH: 27
<212> TYPE: DNA
<213> ORGANISM: GIBCO

<400> SEQUENCE: 5
tggccagaac acaggaggac aggtaag 27

<210> SEQ ID NO 6
<211> LENGTH: 29
<212> TYPE: DNA
<213> ORGANISM: GIBCO

<400> SEQUENCE: 6
gatattcttc agagggctca gactgcttt 29

<210> SEQ ID NO 7
<211> LENGTH: 25
<212> TYPE: DNA
<213> ORGANISM: GIBCO

<400> SEQUENCE: 7
cagactggtc ttgcgggccc attta 25

<210> SEQ ID NO 8
<211> LENGTH: 23
<212> TYPE: DNA
<213> ORGANISM: GIBCO

-continued

```
<400> SEQUENCE: 8

catcctctac ttgatccttc tcc                                               23


<210> SEQ ID NO 9
<211> LENGTH: 226
<212> TYPE: DNA
<213> ORGANISM: IN VITROGEN

<400> SEQUENCE: 9

ccaggcaggc acaagtatgc aaagcatgca tctcaattag tcagcaacca ggtgtggaaa      60

gtccccaggc tccccagcag gcagaagtat gcaaagcatg catctcaatt agtcagcaac     120

catagtcccg cccctaactc cgcccatccc gcccctaact ccgcccagtt ccgcccattc     180

tccgccccat ggctgactaa ttttttttat ttatgcagag gccgag                    226


<210> SEQ ID NO 10
<211> LENGTH: 86
<212> TYPE: DNA
<213> ORGANISM: IN VITROGEN

<400> SEQUENCE: 10

gactaatttt ttttatttat gcagaggccg aggccgcctc tgcctctgag ctattccaga      60

agtagtgacc aggctttttt ggaggc                                            86


<210> SEQ ID NO 11
<211> LENGTH: 131
<212> TYPE: DNA
<213> ORGANISM: IN VITROGEN

<400> SEQUENCE: 11

acttctttat tgcagcttat aatggttaca aataaagcaa tagcatcaca aatttcacaa      60

ataaagcatt tttttcactg cattctagtt ctggtttgtc caaactcatc aatgtatctt     120

atcatgtctg t                                                           131
```